(12) United States Patent
Louwagie

(10) Patent No.: US 9,388,471 B2
(45) Date of Patent: Jul. 12, 2016

(54) METHYLATION OF THE GATA4 GENE IN URINE SAMPLES AS A MARKER FOR BLADDER CANCER DETECTION

(75) Inventor: Joost Louwagie, Liege (BE)

(73) Assignee: MDxHealth SA, Herstal (BE)

(*) Notice: Subject to any disclaimer, the term of this patent is extended or adjusted under 35 U.S.C. 154(b) by 0 days.

(21) Appl. No.: 13/256,365

(22) PCT Filed: Mar. 11, 2010

(86) PCT No.: PCT/EP2010/001546
§ 371 (c)(1),
(2), (4) Date: Sep. 29, 2011

(87) PCT Pub. No.: WO2010/102823
PCT Pub. Date: Sep. 16, 2010

(65) Prior Publication Data
US 2012/0027870 A1 Feb. 2, 2012

Related U.S. Application Data

(60) Provisional application No. 61/160,085, filed on Mar. 13, 2009.

(51) Int. Cl.
*C07H 21/04* (2006.01)
*C12Q 1/68* (2006.01)

(52) U.S. Cl.
CPC ........ *C12Q 1/6886* (2013.01); *C12Q 2600/106* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,786,146 | A * | 7/1998 | Herman et al. | 435/6.12 |
| 7,371,527 | B1 | 5/2008 | Baylin et al. | |
| 2009/0054260 | A1 | 2/2009 | Sidransky | |
| 2010/0144836 | A1 * | 6/2010 | Van Engeland et al. | 514/44 A |

FOREIGN PATENT DOCUMENTS

| | | |
|---|---|---|
| WO | 2008084219 | 7/2008 |
| WO | 2008155549 | 12/2008 |
| WO | WO 2008155549 * | 12/2008 ............ C12Q 1/68 |
| WO | 2009036922 | 3/2009 |
| WO | 2009140666 | 11/2009 |

OTHER PUBLICATIONS

Fu et al. (Cancer Biology and Therapy, vol. 6, No. 10, pp. 1546-1552, 2007).*
Guo et al. (Clinical Cancer Research, vol. 10, pp. 7917-7924, 2004).*
Guo et al (Int. J. Cancer, vol. 199, pp. 2078-2083, 2006).*
Toyota et al. Cancer Research, vol. 59, pp. 4535-4541, Sep. 1999.*
Khulan et al., "Comparative isoschizomer profiling of cystosine methylation: The HELP assay", Genome Research, 2006, 16:1046-1055.
Rein et al., "Identyfing 5-methylcytosine and related modifications in DNA genomes", Nucl. Acids Res., 1998, 26(10):2255-2264.
Thu et al., "Methylated DNA Immunoprecipitation", J. Vis. Exp., 2009, 23:935.
Examination Report for EP10708144.0 dated Jun. 26, 2014.
Brait et al., "Aberrant promoter methylation of multiple genes during pathogenesis of bladder cancer", Cancer Epidemiology Biomarkers & Prevention, Oct. 2008, 17(10):2786-2794.
Cairns et al., "Gene methylation and early detection of genitourinary cancer: the road ahead", Nature Reviews Cancer, Jul. 2007, 7(7):531-543.
Matsubayashi et al., "DNA methylation alterations in the pancreatic juice of patients with suspected pancreatic disease", Cancer Research, Jan. 15, 2006, 66(2):1208-1217.
Van Oers et al., "A simple and fast method for the simultaneous detection of nine fibroblast growth factor receptor 3 mutations in bladder cancer and voided urine", Clinical Cancer Research: an official journal of the American Association for Cancer Research, Nov. 1, 2005, 11(21):7743-7748.
Weisenberger et al., "DNA methylation analysis by digital bisulfite genomic sequencing and digital MethyLight", Nucleic Acids Research, Aug. 2008, 36(14):4689-4698.
International Search Report for PCT/US2010/001546, dated Jun. 2, 2010.
Written Opinion for PCT/US2010/001546, dated Jun. 2, 2010.

* cited by examiner

*Primary Examiner* — Jeanine A Goldberg
(74) *Attorney, Agent, or Firm* — Andrus Intellectual Property Law, LLP

(57) ABSTRACT

A method of detecting a predisposition to, or the incidence of, bladder cancer in a sample comprises detecting an epigenetic change in at least one gene selected from FOXE1 and GATA4. Detection of the epigenetic change is indicative of a predisposition to, or the incidence of, bladder cancer. The sample comprises nucleic acid molecules from bladder cells. The methods may be used to select treatments and patients for treatment. Related kits include primers allowing the methylation status of the genes to be determined.

12 Claims, 1 Drawing Sheet

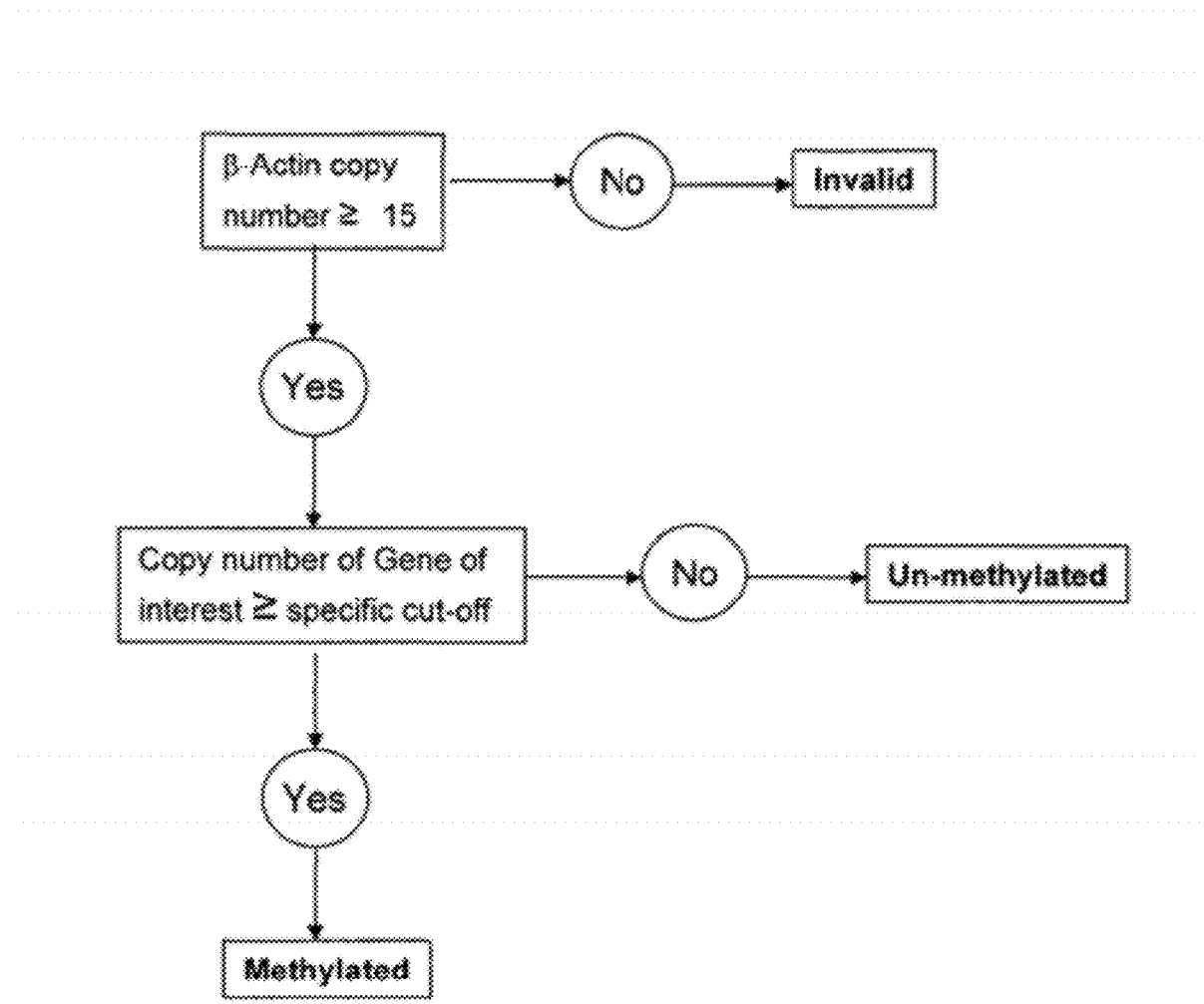

SEQUENCE LISTING

```
<160> NUMBER OF SEQ ID NOS: 26

<210> SEQ ID NO 1
<211> LENGTH: 42
<212> TYPE: DNA
<213> ORGANISM: Artificial sequence
<220> FEATURE:
<223> OTHER INFORMATION: Probe

<400> SEQUENCE: 1
cgactgcgtg tggggtggtg atggaggagg tttaggcagt cg                    42

<210> SEQ ID NO 2
```

```
<211> LENGTH: 26
<212> TYPE: DNA
<213> ORGANISM: Artificial sequence
<220> FEATURE:
<223> OTHER INFORMATION: Primer

<400> SEQUENCE: 2
tagggagtat ataggttggg gaagtt                                          26

<210> SEQ ID NO 3
<211> LENGTH: 27
<212> TYPE: DNA
<213> ORGANISM: Artificial sequence
<220> FEATURE:
<223> OTHER INFORMATION: Primer

<400> SEQUENCE: 3
aacacacaat aacaaacaca aattcac                                         27

<210> SEQ ID NO 4
<211> LENGTH: 36
<212> TYPE: DNA
<213> ORGANISM: Artificial sequence
<220> FEATURE:
<223> OTHER INFORMATION: Probe

<400> SEQUENCE: 4
cgacatgcac gacgcccccg aacctaacgc atgtcg                               36

<210> SEQ ID NO 5
<211> LENGTH: 19
<212> TYPE: DNA
<213> ORGANISM: Artificial sequence
<220> FEATURE:
<223> OTHER INFORMATION: Primer

<400> SEQUENCE: 5
gttatggcga tgcggtttc                                                  19

<210> SEQ ID NO 6
<211> LENGTH: 27
<212> TYPE: DNA
<213> ORGANISM: Artificial sequence
<220> FEATURE:
<223> OTHER INFORMATION: Primer

<400> SEQUENCE: 6
aacacacaat aacaaacaca aattcac                                         27

<210> SEQ ID NO 7
<211> LENGTH: 44
<212> TYPE: DNA
<213> ORGANISM: Artificial sequence
<220> FEATURE:
<223> OTHER INFORMATION: Probe

<400> SEQUENCE: 7
cgtctcgtcg gggttcgggc gtatttttt aggtaggcga gacg                       44

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
```

-continued

<210> SEQ ID NO 9
<211> LENGTH: 23
<212> TYPE: DNA
<213> ORGANISM: Artificial sequence
<220> FEATURE:
<223> OTHER INFORMATION: Primer

<400> SEQUENCE: 9
taacgctata aaactcctac cgc                                    23

<210> SEQ ID NO 10
<211> LENGTH: 40
<212> TYPE: DNA
<213> ORGANISM: Artificial sequence
<220> FEATURE:
<223> OTHER INFORMATION: Probe

<400> SEQUENCE: 10
cgacatgcct cgcgactcga atccccgacc cagcatgtcg                  40

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
aggttagtta gcgttttagg gtc                                    23

<210> SEQ ID NO 12
<211> LENGTH: 19
<212> TYPE: DNA
<213> ORGANISM: Artificial sequence
<220> FEATURE:
<223> OTHER INFORMATION: Primer

<400> SEQUENCE: 12
acgacgacga aacctctcg                                         19

<210> SEQ ID NO 13
<211> LENGTH: 39
<212> TYPE: DNA
<213> ORGANISM: Artificial sequence
<220> FEATURE:
<223> OTHER INFORMATION: Probe

<400> SEQUENCE: 13
cgacatgggt tcgtaaggtt tggggtagcg gccatgtcg                   39

<210> SEQ ID NO 14
<211> LENGTH: 25
<212> TYPE: DNA
<213> ORGANISM: Artificial sequence
<220> FEATURE:
<223> OTHER INFORMATION: Primer

<400> SEQUENCE: 14
gcggttttta aggagtttta ttttc                                  25

<210> SEQ ID NO 15
<211> LENGTH: 21
<212> TYPE: DNA (tttgttcgtt tttcgattgt tc  22 — appears before SEQ ID NO 9)

```
<213> ORGANISM: Artificial sequence
<220> FEATURE:
<223> OTHER INFORMATION: Primer

<400> SEQUENCE: 15
ctacgaaatt ccctttacgc t                                              21

<210> SEQ ID NO 16
<211> LENGTH: 38
<212> TYPE: DNA
<213> ORGANISM: Artificial sequence
<220> FEATURE:
<223> OTHER INFORMATION: Probe

<400> SEQUENCE: 16
cgacatgccg gcggggaagg aaatcgtttc gcatgtcg                            38

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
gttagggttc gggggcgttg tt                                             22

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
ccgtcgcctt cctccgacga a                                              21

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
tcgtcatctg ccccacaga g                                               21

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
ttctgccccc acagagcgct                                                20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
ttctgccccc acagagcgct                                                20
```

```
<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
tggtggaggc tgacgaggcg                                            20

<210> SEQ ID NO 23
<211> LENGTH: 19
<212> TYPE: DNA
<213> ORGANISM: Artificial sequence
<220> FEATURE:
<223> OTHER INFORMATION: Primer

<400> SEQUENCE: 23
tacgaggcgg gcagtgtgt                                             19

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
tcctgttcat cctggtggtg g                                          21

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
tgcacaacct cgactactac aag                                        23

<210> SEQ ID NO 26
<211> LENGTH: 23
<212> TYPE: DNA
<213> ORGANISM: Artificial sequence
<220> FEATURE:
<223> OTHER INFORMATION: Primer

<400> SEQUENCE: 26
tcacaacctc gactactaca aga                                        23
```

METHYLATION OF THE GATA4 GENE IN URINE SAMPLES AS A MARKER FOR BLADDER CANCER DETECTION

CROSS REFERENCE TO RELATED APPLICATION

The present application is the U.S. National Stage Application of International Application PCT/EP2010/001546, filed Mar. 11, 2010, which application was published on Sep. 16, 2010, as International Publication WO 2010/102823, in the English language. The International Application claims the benefit of priority to U.S. Provisional Patent Application No. 61/160,085, filed Mar. 13, 2009, the contents of which applications are incorporated herein by reference in their entireties.

FIELD OF THE INVENTION

The present invention relates to methods and kits for detecting the presence of cancer cells, or the presence of genomic DNA from cancer cells, which include determining the methylation status, or the expression levels, or a combination thereof, of one or more genes. In particular the invention relates to the detection of bladder cancer. The invention also relates to pharmacogenetic methods for determining suitable treatment regimens for cancer and methods for treating cancer patients.

BACKGROUND OF THE INVENTION

Epigenetics can be described as a stable alteration in gene expression potential that takes place during development and cell proliferation, mediated by mechanisms other than alterations in the primary nucleotide sequence of a gene. Three related mechanisms that cause epigenetic alteration in gene expression are DNA methylation, histone code changes and RNA interference.

DNA methylation is the main epigenetic modification in humans. It is a chemical modification of DNA performed by enzymes called methyltransferases, in which a methyl group (m) is added to specific cytosine (C) residues in DNA. In mammals, methylation occurs only at cytosine residues adjacent to a guanosine residue, i.e. at the sequence CG or at the CpG dinucleotide. In normal cells, methylation occurs predominantly in regions of DNA that have few CG base repeats, while CpG islands, regions of DNA that have long repeats of CG bases, remain non-methylated. Gene promoter regions that control protein expression are often CpG island-rich. Aberrant methylation of these normally non-methylated CpG islands in the promoter region causes transcriptional inactivation or silencing of certain functional genes in human cancers (Jones 2002).

Diagnostic markers for cancer detection have been described. One can distinguish between immunological markers and genetic markers. Genetic markers are based on detection of mutation in distinct genes, in particular in tumor suppressor genes. More recently, DNA methylation markers have been evaluated as potential genetic markers for detection of cancer because they offer certain advantages when compared to mutation markers. One of the most important features is that they occur at the early stages of cancer development and in many cases are tissue- and tumor-type specific (Esteller et al. 2001). A further advantage is that the methylation profile is preserved in purified isolated DNA and methylation changes appear to precede apparent malignancy in many cases. In addition, methylation markers may serve predictive purposes as they often reflect the sensitivity to therapy or duration of patient survival. All of these features find their application in improved cancer detection and therapy.

An early diagnosis is critical for the successful treatment of many types of cancer. The traditional methods of diagnosis (such as cytology, histopathology, immunohistochemistry, serology, and so on) are useful, but molecular markers can further subclassify the tumors and identify predisposition to cancer. If the exact methylation profiles of tumors are available and drugs targeting the specific genes are obtainable, then the treatment of cancer could be more focused and rational. Therefore, the detection and mapping of novel methylation markers is an essential step towards improvement of cancer prevention, screening and treatment.

Each year in the U.S. and EU, bladder cancer is diagnosed in >160,000 men and results in >48,000 deaths. While the five-year survival rate for early-stage bladder cancer is high, over 25% present with advanced disease and around 70% experience recurrence or progression following treatment. Urine cytology and cystoscopy are the current standard-of-care for bladder cancer detection and surveillance. Cystoscopy is highly sensitive but is invasive, expensive and causes significant patient discomfort. Urinary cytology is the most widely used method for non-invasive detection with up to 100% specificity. Unfortunately, this method is limited by its sensitivity, which is especially poor for low-grade bladder tumours.

Several methods have been reported for the detection of tumour cells in voided urine. However, none of these urinary tests can replace cystoscopy due to their poor specificity. Combining different methods of bladder cancer detection has been shown to improve sensitivity but unfortunately at the expense of specificity (Lotan Y et al., 2003).

Activating mutations in the fibroblast growth factor receptor 3 (FGFR3) gene have been reported in >50% of primary bladder tumors (van Rhijn B W G et al., 2003). Most of the somatic mutations found in bladder cancer are identical to germ line mutations responsible for skeletal disorders such as thanatophoric dysplasia and achondroplasia (van Rhijn B W G et al., 2002). It has been reported that FGFR3 mutations are very frequent in bladder tumors of low stage and grade, indicating that they occur much more frequently in superficial bladder cancer than in invasive bladder cancer (Billerey C et al., 2001). Recently the development of a new method for FGFR3 mutation analysis based on the detection of single nucleotide changes has been described by van Oers et al. With this method, the nine most common mutations can be detected in one assay simultaneously.

BRIEF DESCRIPTION OF THE INVENTION

The invention, as set out in the claims, is based around the discovery of specific genes and panels of genes whose methylation status is linked to predisposition to, or the incidence of bladder cancer. Use of these genes for detecting bladder cancer, in particular in the context of appropriate tissue or urine samples, has been shown to produce highly sensitive and specific results.

Accordingly, the invention provides a method of detecting a predisposition to, or the incidence of, bladder cancer in a sample, the sample comprising nucleic acid molecules from bladder cells, the method comprising detecting an epigenetic change in at least one gene selected from FOXE1 and GATA4, wherein detection of the epigenetic change is indicative of a predisposition to, or the incidence of, bladder cancer.

The most preferred epigenetic change which is detected comprises, consists essentially of or consists of methylation. In particular, aberrant methylation, which may be referred to as hypermethylation, of the gene or genes is detected.

Epigenetic loss of gene function can be rescued by the use of DNA demethylating agents and/or DNA methyltransferase inhibitors and/or HDAC inhibitors. In one aspect, the invention provides a method for predicting the likelihood of successful treatment of bladder cancer with a DNA demethylating agent and/or a DNA methyltransferase inhibitor and/or HDAC inhibitor comprising detecting an epigenetic change in at least one gene selected from FOXE1 and GATA4 wherein detection of the epigenetic change is indicative that the likelihood of successful treatment is higher than if the epigenetic modification is not detected. Similarly, the invention provides a method for predicting the likelihood of resistance to treatment of bladder cancer with a DNA demethylating agent and/or DNA methyltransferase inhibitor and/or HDAC inhibitor comprising detecting an epigenetic change in at least one gene selected from FOXE1 and GATA4, wherein detection of the epigenetic change is indicative that the likelihood of resistance to treatment is lower than if the epigenetic modification is not detected.

Epigenetic loss of gene function can identify the need for treatment which may differ according to the type of carcinoma. Therefore, the present invention also relates to a method of selecting a suitable treatment regimen for bladder cancer comprising detecting an epigenetic change in at least one gene selected from FOXE1 and GATA4, wherein detection of the epigenetic change results in selection of a DNA demethylating agent and/or a DNA methyltransferase inhibitor and/or a HDAC inhibitor for treatment and wherein if the epigenetic change is not detected, a DNA demethylating agent and/or a DNA methyltransferase inhibitor and/or a HDAC inhibitor is not selected for treatment.

In a related aspect, the invention provides a method for determining suitable treatment of a transitional cell carcinoma or squamous cell carcinoma comprising (in a sample obtained from a subject), determining the methylation status of at least one gene selected from FOXE1 and GATA4, in a transitional cell tumor or squamous cell carcinoma, wherein if the at least one gene is methylated, in particular hypermethylated, the need for resection of the transitional cell carcinoma or squamous cell carcinoma is identified.

In an opposite scenario, the invention provides for a method for determining suitable treatment of a transitional cell carcinoma or squamous cell carcinoma comprising (in a sample obtained from a subject), determining the methylation status at least one gene selected from FOXE1 and GATA4, in a transitional cell tumor or squamous cell carcinoma, wherein if the at least one gene is unmethylated or methylated to a lesser degree, it is determined that there is no need for resection of the transitional cell or squamous cell tumor.

In a further related aspect, the invention provides a method of treating bladder cancer in a subject comprising administration of a DNA demethylating agent and/or a DNA methyltransferase inhibitor wherein the subject has been selected for treatment on the basis of a method of the invention.

The invention also relates to a kit for detecting a predisposition to, or the incidence of, bladder cancer in a sample comprising:
(a) means for detecting an epigenetic change in at least one gene selected from FOXE1 and GATA4
(b) means for processing a urine sample.

The invention also provides a kit for detecting a predisposition to, or the incidence of, bladder cancer in a sample comprising at least one primer pair for determining the methylation status of each gene in a panel of genes wherein the panel of genes comprises, consists essentially of or consists of a panel of genes selected from FOXE1 and TWIST1, FOXE1, TWIST1 and NID2, FOXE1, CCNA2 and NID2, GATA4 and NID2, GATA4, NID2 and TWIST1; or CCNA1, NID2 and GATA4 or FOXE1 and GATA4.

DETAILED DESCRIPTION OF THE INVENTION

The present invention is based on the discovery that cytosines within CpG dinucleotides in at least one gene selected from FOXE1 and GATA4 are differentially methylated in human cancer tissue and urine samples versus normal human tissue and urine samples, more in particular in bladder tissue and/or urine samples (containing bladder cell-derived nucleic acid molecules).

The invention provides in a first aspect a method of detecting a predisposition to, or the incidence of, bladder cancer in a sample, the sample comprising nucleic acid molecules from bladder cells, the method comprising detecting an epigenetic change in at least one gene selected from FOXE1 and GATA4, wherein detection of the epigenetic change is indicative of a predisposition to, or the incidence of, bladder cancer.

The invention may involve detecting an epigenetic change in a panel of genes comprising at least one of the genes together with one, two, three, four or five additional genes, wherein detection of an epigenetic change in at least one of the genes in the panel is indicative of a predisposition to, or the incidence of, bladder cancer. Thus, the additional genes also act as markers for bladder cancer, in that detection of an epigenetic change is indicative of a predisposition to, or the incidence of, bladder cancer. In some embodiments, an epigenetic change in at least two or three genes is detected. In certain embodiments, the additional genes are selected from TWIST1, NID2 and CCNA1.

In certain embodiments the panel of genes comprises, consists essentially of or consists of a panel of genes selected from FOXE1 and TWIST1; FOXE1, TWIST1 and NID2; FOXE1, CCNA2 and NID2, GATA4 and NID2, GATA4, NID2 and TWIST1; CCNA1, NID2 and GATA4 or FOXE1 and GATA4. These panels of genes have been shown to produce improved levels of sensitivity of detection of bladder cancer, in particular in urine samples. The detection of an epigenetic change in each of the panel of genes may be carried out in a single reaction. Methods are known in the art for carrying out such multiplexing. Distinguishable labels (on primers or probes), such as labels with fluoresce at different wavelengths, or primers which generate different sized amplification products may be employed, for example.

"CCNA1" is the standard nomenclature for cyclin A1 (Accession numbers: ENSG00000133101, U66838, NM_003914); "FOXE1" for forkhead box E1 (thyroid transcription factor 2) (Accession number: U89995 and ENSG00000178919); "GATA4" for GATA binding protein 4 (Accession numbers: ENSG00000136574, AK097060 and NM_002052); "NID2" for nidogen 2 (osteonidogen) (Accession numbers: ENSG00000087303; AB009799); and "TWIST1" for twist homolog 1 (*Drosophila*) (Accession numbers: ENSG00000122691, U80998, NM_000474), as approved by the Human Genome Organisation. "FGFR3" is the approved nomenclature for fibroblast growth factor receptor 3 (located on chromosome 4p16.3, accession number M64347).

By "gene" is meant not only the particular sequences found in the publicly available database entries, but also encompasses transcript and nucleotide variants of these sequences. The term may also encompass any gene which is taken from the family to which the named "gene" belongs with the proviso that methylation or another epigenetic modification of the "gene" is linked to bladder cancer.

The methods of the invention are preferably ex vivo or in vitro methods carried out on a test sample. The methods are non-invasive. The methods may be used to identify any type of bladder cancer.

The "sample" in which to detect epigenetic silencing of the at least one gene selected from FOXE1 and GATA4 is a sample comprising nucleic acid molecules from bladder cells. Thus the sample may include bladder cells and/or may include nucleic acid molecules, in particular (genomic) DNA, derived from bladder cells. The sample may thus be a tissue sample, body fluid, body fluid precipitate or lavage specimen. Preferably, the test sample is obtained from a human subject. Test samples for diagnostic, prognostic, or personalised medicinal uses can be obtained from surgical samples, such as biopsies or fine needle aspirates, from paraffin embedded tissues, from frozen tumor tissue samples, from fresh tumor tissue samples, from a fresh or frozen body fluid, for example. Non-limiting examples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens.

The test sample may be taken from a human subject and contains (transitional) bladder cells or nucleic acid from (transitional) bladder cells. Alternatively, the test sample contains squamous carcinoma bladder cells or nucleic acid from squamous cell carcinomas. The sample may be obtained from a bladder tissue. In specific embodiments, the test sample comprises, consists essentially of or consists of a urine sample or is derived from urine. The sample may contain nucleic acid from transitional bladder cells or squamous carcinoma bladder cells. The test sample can be derived from liquid urine, a precipitate thereof, or a precipitate in the urine. The tissues and body fluids may be collected using any suitable methods, many of which are well known in the art. The "nucleic acid" in the methods according to the invention is preferably deoxyribonucleic acid (DNA), in particular genomic DNA.

In embodiments where urine samples are employed, they may be processed according to any suitable procedure. In certain embodiments, the methods of the invention additionally comprise stabilising the urine sample. It is shown herein that stabilising the urine sample, by adding a suitable stabilizing buffer to the urine, may avoid the need for centrifugation of the urine sample shortly after obtaining the sample. Typically centrifugation occurs within 4 hours of obtaining the urine sample in order to maintain the integrity of the DNA (in particular in the sediment fraction). The samples can be maintained at room temperature for up to 48 or 72 hours or more following addition of a stabilizing buffer, without the requirement for centrifugation. This advantageously permits home collection of urine samples and also removes the necessity for centrifugation equipment at each collection site. Thus, the methods of the invention may incorporate methods for conveniently storing urine samples for a period of up to 72 (or 48) hours or more at room temperature, such as at least 4, 12, 24, 36 or 48 hours up to 72 hours or more, comprising adding a stabilising buffer to the urine sample, with the proviso that the urine sample is not centrifuged or otherwise fractionated prior to or during the storage period and storing the urine for this period. The urine sample can be stored according to these methods for longer periods than 72 hours provided that the integrity of the DNA in the sample is maintained (thus allowing the methods of the invention to be carried out). Following the storage period, the sample may then be centrifuged as part of the methods of the invention. The thus centrifuged sample may be stored under appropriate conditions, as discussed herein, such as at 4° C. or at −20° C. Suitable stabilizing buffers for use in these methods are described herein. Any suitable stabilizing buffer may be employed.

Whilst stabilization may be achieved via any suitable means, in certain embodiments, stabilisation occurs through addition of a stabilising buffer. The stabilising buffer incorporates suitable components to maintain DNA integrity in the urine sample and/or to maintain the quality of the urine sample as a whole. Thus, the methods and kits of the invention may employ a stabilising buffer solution for storing urine samples comprising EDTA and/or DMSO and/or an antibacterial and/or one or more STABILUR™ tablets. Use of STABILUR™ tablets has been shown to be particularly effective in the methods of the invention. Thus, the stabilising buffer may contain or comprise an appropriate mixture of buffering and osmolarity adjustment ingredients. In specific embodiments, the stabilising buffer comprises EDTA, an antibacterial and optionally a STABILUR™ tablet. This solution may be used for storing a urine sample at a temperature of around 4° C. or at other temperatures, such as room temperature. In other embodiments, the methods and kits of the invention may employ a stabilising buffer for storing urine samples comprising EDTA, DMSO and an antibacterial. The solution may be used for storing a urine sample under freezing conditions or at other temperatures, such as room temperature. These buffer solutions are useful for storing whole urine samples. They are useful for storing the cell-free DNA component from a urine sample and/or the pellet fraction produced typically by (low speed) centrifugation. Typically, the stabilising buffer is added to the urine sample shortly after collection of the sample. This is then stored, according to the methods described herein, for up to 72 hours or more prior to centrifugation. The sample may then be centrifuged prior to further processing according to the methods of the invention. Following centrifugation, the samples—such as the sediment and/or or pellet portion of the sample—may then be stored for longer periods of time, for example at a temperature such as −20° C. for up to 6 months or longer.

The stabilising buffer for use in methods of the invention may comprise, consist essentially of or consist of at least one component selected from EDTA, an antibacterial, DMSO and STABILUR™ tablets. STABILUR tablets are available from Cargille Labs and contain appropriate mixtures of buffering and osmolarity adjustment ingredients. Suitable equivalents to this product may be utilised as appropriate, such as preservative tubes available from CellSave (CellSave Preservative Tubes).

The term "antibacterial" is intended to cover any compound, molecule or otherwise which has an inhibitory effect on the growth or viability of one or more bacteria. Both biological and non-biological molecules are intended to fall within the definition. In certain embodiments, the anti-bacterial comprises, consists essentially of or consists of an antibiotic. Many antibiotics are well known in the art and commercially available. Mixtures of antibiotics may be utilised as appropriate, such as the Antibiotic-Antimycotic A5955-100 ml antibiotic mix available from Sigma-Aldrich.

Suitable anti-bacterials may include cytokines such as interferons and interleukins and derivatives and mimetics thereof, and "small molecules". A small molecule is defined as a molecular entity with a molecular weight of less than 1500 daltons, preferably less than 1000 daltons. The small molecule may for example be an organic, inorganic or organometallic molecule, which may also be in the form or a suitable salt, such as a water-soluble salt; and may also be a complex, chelate and/or a similar molecular entity, as long as its (overall) molecular weight is within the range indicated above.

In specific embodiments the EDTA is present at a final concentration of around 10 mM and/or the DMSO is present at around 10% of the final stabilising buffer volume.

Samples (to which a stabilising buffer has been added) may be stored at any suitable temperature, including room temperature. For example, the storage temperature may be anywhere between approximately −50° C. and approximately 37° C., preferably approximately −10° C. to −30° C., such as approximately −20° C. or approximately 1° C. to 10° C., such as approximately 4° C. By "freezing" is meant a temperature at or below 0° C., preferably approximately −20° C.

The methods of the invention may also include the step of obtaining the test sample in some embodiments. The tissue sample or liquid sample comprising the bladder-cell derived nucleic acid molecules may be lysed or need to be concentrated to create a mixture of biological compounds comprising nucleic acids and other components. Alternatively, the nucleic acid may need to be cleared of proteins or other contaminants, e.g. by treatment with proteinase K. Procedures for lysing or concentrating biological samples are known by the person skilled in the art and can be chemical, enzymatic or physical in nature. A combination of these procedures may be applicable in some embodiments. For instance, lysis may be performed using ultrasound, high pressure, shear forces, alkali, detergents or chaotropic saline solutions, or proteases or lipases. For the lysis procedure to obtain nucleic acids, or concentrating nucleic acid from samples, reference may be made to Sambrook, J., et al., Molecular cloning: A Laboratory Manual, (2001) 3rd edition, Cold Spring Harbor Laboratory Press, Cold Spring Harbor, N.Y. and Ausubel, F. M., et al., Current Protocols in Molecular Biology (1987), J. Wiley and Sons, New York. In certain embodiments, nucleic acids are extracted from the test sample using a commercially available purification kit, such as the PUREGENE® DNA purification kit. In specific embodiments, the sample may be centrifuged and nucleic acid purified from the sediment or pellet fraction, in particular using such a purification kit. Suitable purification kits are commercially available and would be well known to one skilled in the art.

The test sample is generally obtained from a (human) subject suspected of being tumorigenic. Alternatively the test sample is obtained from a subject undergoing routine examination and not necessarily being suspected of having a disease. Thus patients at risk can be identified before the disease has a chance to manifest itself in terms of symptoms identifiable in the patient. Alternatively the sample is obtained from a subject undergoing treatment, or from patients being checked for recurrence of disease.

"Detecting" a disease or predisposition to disease is defined herein to include detecting by way of routine examination, screening for a disease or pre-stadia of a disease, monitoring and/or staging the state and/or progression of the disease, checking for recurrence of disease following treatment and monitoring the success of a particular treatment. The detection can also have prognostic value, and the prognostic value of the tests can be used as a marker of potential susceptibility to cancer. The detection may also link to a cancer stage or grade. The "Stage" refers to how far a cancer has progressed anatomically, while the "grade" refers to cell appearance (differentiation) and DNA make up.

"Cancer" refers to the presence of cells possessing characteristics typical of cancer-causing cells, such as uncontrolled proliferation, immortality, metastatic potential, rapid growth and proliferation rate, and certain characteristic morphological features. The particular cancer type relevant to the invention is bladder cancer.

"Bladder cancer" is defined to include transitional cell carcinoma or squamous cell carcinomas. The cancer may comprise superficial bladder cancer, invasive bladder cancer, or metastatic bladder cancer. Superficial cancer is only in cells in the lining of the bladder and has high grade of recurrence. A superficial tumor may grow through the lining into the muscular wall of the bladder and become invasive cancer. Invasive cancer can extend through the bladder wall and can grow into a nearby organ such as the uterus or vagina (in women) or the prostate gland (in men). It also may invade the wall of the abdomen. The cancer becomes metastatic when it spreads outside the bladder into nearby lymph nodes and other organs, such as the lungs, liver, or bones. Various stages of bladder cancer to which the invention is applicable are listed in the tables in the experimental section herein.

"Epigenetic change" is defined to include herein alterations resulting in diminished gene expression potential, mediated by mechanisms other than alterations in the primary nucleotide sequence of a gene. Three related mechanisms that cause epigenetic alteration in gene expression are DNA methylation, histone code changes and RNA interference. The epigenetic change is generally epigenetic silencing in this invention. Epigenetic silencing may be caused by DNA methylation in certain embodiments.

The epigenetic change in the genes of present invention is generally epigenetic silencing caused by (aberrant) DNA methylation. Thus, the invention provides for a method of detecting a predisposition to, or the incidence of, bladder cancer in a sample comprising detecting epigenetic silencing in at least one gene selected from FOXE1 and GATA4, wherein epigenetic silencing of the at least one gene is detected by determination of the methylation status of the gene and wherein methylation of the gene (which may be considered aberrant methylation or hypermethylation) is indicative of a predisposition to, or the incidence of, bladder cancer.

The term "methylation status" refers to the presence or absence of a methylated cytosine residue in one or more CpG dinucleotides within the nucleic acid or gene of interest. In many genes, the CpG islands are found in the promoter region and may begin (just) upstream of a promoter and extend downstream into the transcribed region. Methylation of a CpG island at a promoter often prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g. exons), downstream of coding regions in, for example, enhancer regions, and in introns. All of these regions can be assessed to determine their methylation status, as appropriate. In certain embodiments, the methylation status of the gene is assessed by determining levels of methylation in the promoter, intron, exon1 and/or exon2 region of the gene. A "promoter" is a region upstream from the transcription start site (TSS), extending between approximately 10 Kb, 4 Kb, 3 Kb, 1 Kb, 500 bp or 150 to 300 bp from the TSS. When the CpG distribution in the promoter region is rather scarce, levels of methylation may be assessed in the intron and/or exon regions. The region for assessment may be a region that comprises both intron and exon sequences and thus overlaps both regions. CpG islands are readily identifiable through a range of techniques, including sequencing and in silico predictive methods.

More specifically, the methods of the invention may investigate an epigenetic change, and in particular the methylation status, of the relevant gene or genes around the TSS, the genomic location of which is shown in Table 1 (based upon publicly available human genome sequence information—from Ensembl) for each of the relevant genes. In certain embodiments, the methods of the invention may investigate an epigenetic change, and in particular the methylation status within, or between, and optionally including, the primer binding sites of the primers listed in the table. In specific embodiments, the methods may investigate an epigenetic change, and in particular the methylation status, within or between the genomic locations listed in Table 1 (see the column entitled "location of the assay"). Thus, for example, the methods may investigate the genomic region between (and including) nucleotide 99655269 and nucleotide 99655174 for FOXE1 and/or the genomic region between (and including) nucleotide 11599063 and nucleotide 11599169 for GATA4.

Determination of the methylation status may be achieved through any suitable means. Suitable examples include bisulphite genomic sequencing and/or by methylation specific PCR. Various techniques for assessing methylation status are known in the art and can be used in conjunction with the present invention: sequencing, methylation-specific PCR (MS-PCR), melting curve methylation-specific PCR(McMS-PCR), MLPA with or without bisulphite treatment, QAMA (Zeschnigk et al, 2004), MSRE-PCR (Melnikov et al, 2005), MethyLight (Eads et al., 2000), ConLight-MSP (Rand et al., 2002), bisulphite conversion-specific methylation-specific PCR (BS-MSP) (Sasaki et al., 2003), COBRA (which relies upon use of restriction enzymes to reveal methylation dependent sequence differences in PCR products of sodium bisulphite-treated DNA), methylation-sensitive single-nucleotide primer extension conformation (MS-SNuPE), methylation-sensitive single-strand conformation analysis (MS-SSCA), Melting curve combined bisulphite restriction analysis (Mc-COBRA) (Akey et al., 2002), PyroMethA, HeavyMethyl (Cottrell et al. 2004), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR. A review of some useful techniques for DNA methylation analysis is provided in Nucleic acids research, 1998, Vol. 26, No. 10, 2255-2264, Nature Reviews, 2003, Vol. 3, 253-266; Oral Oncology, 2006, Vol. 42, 5-13, which references are incorporated herein in their entirety.

Techniques for assessing methylation status are based on distinct approaches. Some include use of endonucleases. Such endonucleases may either preferentially cleave methylated recognition sites relative to non-methylated recognition sites or preferentially cleave non-methylated relative to methylated recognition sites. Some examples of the former are Acc III, Ban I, BstN I, Msp I, and Xma I. Examples of the latter are Acc II, Ava I, BssH II, BstU I, Hpa II, and Not I. Differences in cleavage pattern are indicative for the presence or absence of a methylated CpG dinucleotide. Cleavage patterns can be detected directly, or after a further reaction which creates products which are easily distinguishable. Means which detect altered size and/or charge can be used to detect modified products, including but not limited to electrophoresis, chromatography, and mass spectrometry.

Alternatively, the identification of methylated CpG dinucleotides may utilize the ability of the methyl binding domain (MBD) of the MeCP2 protein to selectively bind to methylated DNA sequences (Cross et al, 1994; Shiraishi et al, 1999). The MBD may also be obtained from MBP, MBP2, MBP4, poly-MBD (Jorgensen et al., 2006) or from reagents such as antibodies binding to methylated nucleic acid. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include amongst others methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulphite ions. The methods of the invention may use bisulphite ions, in certain embodiments. The bisulphite conversion relies on treatment of DNA samples with sodium bisulphite which converts unmethylated cytosine to uracil, while methylated cytosines are maintained (Furuichi et al., 1970). This conversion finally results in a change in the sequence of the original DNA. It is general knowledge that the resulting uracil has the base pairing behaviour of thymidine which differs from cytosine base pairing behaviour. This makes the discrimination between methylated and non-methylated cytosines possible. Useful conventional techniques of molecular biology and nucleic acid chemistry for assessing sequence differences are well known in the art and explained in the literature. See, for example, Sambrook, J., et al., Molecular cloning: A laboratory Manual, (2001) 3rd edition, Cold Spring Harbor, N.Y.; Gait, M. J. (ed.), Oligonucleotide Synthesis, A Practical Approach, IRL Press (1984); Hames B. D., and Higgins, S. J. (eds.), Nucleic Acid Hybridization, A Practical Approach, IRL Press (1985); and the series, Methods in Enzymology, Academic Press, Inc.

Some techniques use primers for assessing the methylation status at CpG dinucleotides. Two approaches to primer design are possible. Firstly, primers may be designed that themselves do not cover any potential sites of DNA methylation. Sequence variations at sites of differential methylation are located between the two primers and visualisation of the sequence variation requires further assay steps. Such primers are used in bisulphite genomic sequencing, COBRA, Ms-SnuPE and several other techniques. Secondly, primers may be designed that hybridize specifically with either the methylated or unmethylated version of the initial treated sequence. After hybridization, an amplification reaction can be performed and amplification products assayed using any detection system known in the art. The presence of an amplification product indicates that a sample hybridized to the primer. The specificity of the primer indicates whether the DNA had been modified or not, which in turn indicates whether the DNA had been methylated or not. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labelled using any detection system known in the art. These include but are not limited to fluorescent moieties, radioisotope labelled moieties, bioluminescent moieties, luminescent moieties, chemiluminescent moieties, enzymes, substrates, receptors, or ligands.

In the MSP approach, DNA may be amplified using primer pairs designed to distinguish methylated from unmethylated DNA by taking advantage of sequence differences as a result of sodium-bisulphite treatment (Herman et al., 1996; and WO 97/46705). For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA. Amplification using a DNA polymerase and a second primer yield amplification products which can be readily observed, which in turn indicates whether the DNA had been methylated or not. Whereas PCR is a preferred amplification method, variants on this basic technique such as nested PCR and multiplex PCR are also included within the scope of the invention.

As mentioned earlier, a preferred embodiment for assessing the methylation status of the relevant gene requires amplification to yield amplification products. The presence of amplification products may be assessed directly using methods well known in the art. They simply may be visualized on a suitable gel, such as an agarose or polyacrylamide gel. Detection may involve the binding of specific dyes, such as ethidium bromide, which intercalate into double-stranded DNA and visualisation of the DNA bands under a UV illuminator for example. Another means for detecting amplification products comprises hybridization with oligonucleotide probes. Alternatively, fluorescence or energy transfer can be measured to determine the presence of the methylated DNA.

A specific example of the MSP technique is designated real-time quantitative MSP (QMSP), and permits reliable quantification of methylated DNA in real time or at end point. Real-time methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labelled primers and/or labelled probes can be used for quantification. They represent a specific application of the well known and commercially available real-time amplification techniques such as TAQMAN®, MOLECULAR BEACONS®, AMPLIFLUOR® and SCORPION®, DzyNA®, Plexor™ etc. In the real-time PCR systems, it is possible to monitor the PCR reaction during the exponential phase where the first significant increase in the amount of PCR product correlates to the initial amount of target template.

Real-Time PCR detects the accumulation of amplicon during the reaction. Real-time methods do not need to be utilised, however. Many applications do not require quantification and Real-Time PCR is used only as a tool to obtain convenient results presentation and storage, and at the same time to avoid post-PCR handling. Thus, analyses can be performed only to confirm whether the target DNA is present in the sample or not. Such end-point verification is carried out after the amplification reaction has finished. This knowledge can be used in a medical diagnostic laboratory to detect a predisposition to, or the incidence of, cancer in a patient. End-point PCR fluorescence detection techniques may employ the same approaches as widely used for Real Time PCR. For example, instruments such as "Gene" detector ("Gene-Machine") allow the measurement of fluorescence directly in PCR tubes (available from Bioron, see http://www.bioron.net/excellent-products-from-bioron/fluorescent-detector.html).

In real-time embodiments, quantitation may be on an absolute basis, or may be relative to a constitutively methylated DNA standard, or may be relative to an unmethylated DNA standard. Methylation status may be determined by using the ratio between the signal of the marker under investigation and the signal of a reference gene where methylation status is known (such as β-actin for example), or by using the ratio between the methylated marker and the sum of the methylated and the non-methylated marker. Alternatively, absolute copy number of the methylated marker gene can be determined.

Suitable controls may need to be incorporated in order to ensure the method chosen is working correctly and reliably. Suitable controls may include assessing the methylation status of a gene known to be methylated. This experiment acts as a positive control to help to ensure that false negative results are not obtained. The gene may be one which is known to be methylated in the sample under investigation or it may have been artificially methylated, for example by using a suitable methyltransferase enzyme, such as Sss1 methyltransferase. In one embodiment, the gene selected from FOXE1 and GATA4, may be assessed in normal (i.e. non-cancerous bladder) cells, following treatment with Sss1 methyltransferase, as a positive control.

Additionally or alternatively, suitable negative controls may be employed with the methods of the invention. Here, suitable controls may include assessing the methylation status of a gene known to be unmethylated or a gene that has been artificially demethylated. This experiment acts as a negative control to ensure that false positive results are not obtained. In one embodiment, the gene selected from FOXE1 and GATA4 may be assessed in normal (bladder) cells as a negative control, since it has been shown for the first time herein that these genes are unmethylated in normal (bladder) tissues.

Whilst PCR is the preferred nucleic acid amplification technique, other amplification techniques may also be utilised to detect the methylation status of the concerned gene. Such amplification techniques are well known in the art, and include methods such as NASBA (Compton, 1991), 3SR (Fahy et al., 1991) and Transcription Mediated Amplification (TMA). Other suitable amplification methods include the ligase chain reaction (LCR) (Barringer et al, 1990), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technology, and nick displacement amplification (WO 2004/067726). This list is not intended to be exhaustive; any nucleic acid amplification technique may be used provided the appropriate nucleic acid product is specifically amplified. Thus, these amplification techniques may be tied in to MSP and/or bisulphite sequencing techniques for example.

In certain embodiments, MSP primers are utilised in the methods of the invention. Primers useful in MSP to determine the methylation status of the genes of interest are set forth in table 1 below. These primers may comprise, consist essentially of or consist of (any of) the nucleotide sequences set forth in the table. Primers of the invention preferably are designed to bind to fully methylated genomic sequences in the regions under investigation.

Further characteristics of these primers are summarized in the experimental part. It is noted that variants of these sequences may be utilised in the present invention. In particular, additional flanking sequences may be added, for example to improve binding specificity, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers and/or probes set forth herein. The primers and probes may incorporate synthetic nucleotide analogues as appropriate or may be DNA, RNA or PNA based for example, or mixtures thereof. Similarly alternative fluorescent donor and acceptor moieties/FRET pairs may be utilised as appropriate. In addition to being labelled with the fluorescent donor and acceptor moieties, the primers and probes may include modified oligonucleotides and other appending groups and labels provided that the functionality as a primer and/or probe in the methods of the invention is not compromised.

The application of the methods of present invention on small amounts of abnormally-methylated DNA, that are released into collected fluids, such as urine, may require the amplification of the DNA of interest before testing for methylation of any specific gene. Suitable methods on whole genome amplification and libraries generation for such amplification (e.g. Methylplex and Enzyplex technology, Rubicon Genomics) are described in US2003/0143599, WO2004/081225 and WO2004/081183. In addition, WO2005/090507 describes library generation/amplification methods that require either bisulphite conversion or non-bisulphite based applications. Bisulphite treatment may occur before or after library construction and may require the use of adaptors resistant to bisulphite conversion. Meth-DOP-PCR (Di Vinci et al, 2006), a modified degenerate oligonucleotide-primed PCR amplification (DOP-PCR) that is combined with MSP, provides another suitable method for specific detection of methylation in small amount of DNA. An initial amplification of the gene or genes of interest, which is non-methylation specific may be carried out prior to the methylation detection method itself. Improved management of patient care may require these existing methods and techniques to supplement the methods of the invention.

Since epigenetic silencing of a gene manifests itself most frequently in diminished expression in tumor cells, the invention provides for a method of detecting bladder cancer or predisposition to bladder cancer comprising detecting epigenetic silencing of at least one gene selected from FOXE1 and GATA4, wherein epigenetic silencing of the at least one gene is determined by measurement of expression levels of the gene and wherein reduced expression of the gene is indicative for cancer or predisposition to cancer. Thus, in certain embodiments, the methods of the invention may comprise, consist essentially of or consist of determining the effect of methylation on expression of the gene or genes of interest. Expression may be compared with gene expression in one or more control cells in which the methylation status and corresponding expression levels are known. Positive and negative controls may be employed as required. In specific embodiments, expression is determined at the RNA level. Any suitable technique may be employed. In certain embodiments, expression at the RNA level is determined by reverse transcriptase polymerase chain reaction (RT-PCR). Methods employing nucleic acid probe hybridization to the relevant transcript(s) of a gene selected from FOXE1 and GATA4 (optionally with additional genes) may be employed for measuring the presence and/or level of mRNA. Such methods include use of nucleic acid probe arrays (microarray technology) and Northern blots. Advances in genomic technologies now permit the simultaneous analysis of thousands of genes, although many are based on the same concept of specific probe-target hybridization. Sequencing-based methods are an alternative. These methods started with the use of expressed sequence tags (ESTs), and now include methods based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

In alternative embodiments, expression is determined at the protein level. Again, any suitable technique may be employed such as western blots, immunohistochemical staining and immunolocalization, immunofluorescence, enzyme-linked immunosorbent assay (ELISA), immunoprecipitation assays, complement fixation assay, agglutination reactions, radioimmunoassay, flow cytometry, mass spectrofotometry, and equilibrium dialysis. These methods generally depend upon a reagent specific for identification of the gene product. The reagent is preferably an antibody and may comprise monoclonal or polyclonal antibodies. Fragments and derivative antibodies may also be utilised, to include without limitation Fab fragments, ScFv, single domain antibodies, nanoantibodies, heavy chain antibodies, aptamers etc. which retain gene product binding function. Any detection method may be employed in accordance with the invention. The nature of the reagent is not limited except that it must be capable of specifically identifying the appropriate gene product.

Of course, in the case of a positive diagnosis of bladder cancer, there will be reduced levels or none of the relevant RNA or protein coded by at least one gene selected from FOXE1 and GATA4. In certain embodiments this will present a negative result. In this case, use of suitable controls ensures that false diagnoses will not be made, for example caused by degraded or non-specific reagents. Thus, the same reagent can be tested on samples in which it is known that the at least one gene selected from FOXE1 and GATA4 is expressed. A positive result in this control sample, combined with a negative result in the test sample provides a confident diagnosis of bladder cancer and removes any doubt over the quality of the reagent.

As a further confirmation of the functional relevance of the methylation, the methods of the invention may further comprise, consist essentially of or consist of determining whether use of a demethylating agent can restore expression of the gene or genes of interest. If the result is positive, this indicates that the methylation is the cause of the loss of expression. Any suitable demethylating agent may be employed, of which many are known. In specific embodiments, the demethylating agent comprises, consists essentially of or consists of 5-aza-2-deoxycytidine.

The decreased level of expression may, as necessary, be measured in order to determine if it is statistically significant in the sample. This helps to provide a reliable test for the methods of the invention. Any method for determining whether the expression level of the gene selected from FOXE1 and GATA4 is significantly reduced may be utilised. Such methods are well known in the art and routinely employed. For example, statistical analyses may be performed using an analysis of variance test. Typical P values for use in such a method would be P values of <0.05 or 0.01 or 0.001 when determining whether the relative expression or activity is statistically significant. A change in expression may be deemed significant if there is at least a 10% decrease for example. The test may be made more selective by making the change at least 15%, 20%, 25%, 30%, 35%, 40% or 50%, for example, in order to be considered statistically significant.

In certain embodiments, the decreased level of expression or activity of the gene selected from FOXE1 and GATA4 is determined with reference to a control sample. This control sample may be taken from normal (i.e. non tumorigenic) tissue in the subject, where expression of the gene selected from FOXE1 and GATA4 is normal. Additionally or alternatively control samples may also be utilised in which there is known to be a lack of expression of the concerned gene. Suitable additional controls may also be included (to ensure that the test is working properly) such as measuring levels of expression or activity of a suitable reference gene in both test and control samples.

Following diagnosis, treatment is often decided according to the stage of a cancer. The "stage" of a cancer is a descriptor (usually numbers I to IV) of how much the cancer has spread. The stage often takes into account the size of a tumor, how deep it has penetrated, whether it has invaded adjacent organs, if and how many lymph nodes it has metastasized to, and whether it has spread to distant organs. Staging of cancer is important because the stage at diagnosis is the biggest predictor of survival, and treatments are often changed based on the stage. For instance, approximately 70% to 80% of patients diagnosed with bladder cancer will present with superficial bladder tumors (stage Ta, T is, or T1). T is tumors, also referred to as CIS (carcinoma in situ), are flat tumors confined to the urothelium but, if left untreated, will likely progress to muscle invasive disease. Tumors that are T2 and T3 are indicative of invasion into the bladder muscle or fat. Stage 4 tumors represent those that have invaded the pelvic or abdominal wall or have metastasized to adjacent organs.

All methods of the present invention are preferentially used in connection with bladder cancer. To attain high rates of tumor detection, it may be advantageous to complement the methods of the invention with established methods for bladder cancer identification. Non-invasive methods may be especially suitable for use in combination with the non-invasive methods of the invention. Methods of the present invention may be used in conjunction with one or more of the following methods:

Urinalysis

Urine cytology (microscopic exam of urine to look for cancerous cells)

Cystoscopy (use of lighted instrument to view inside of bladder. Diagnosis and staging of bladder cancer begins with cystoscopy)

Bladder biopsy (usually performed during cystoscopy)

Intravenous pyelogram—IVP (Dyes are injected into the bloodstream, which allow for better visualization of any tumors or abnormalities in the bladder using routine X-rays.)

Imaging Techniques: X-ray imaging of the upper urinary tract (including the ureters and kidneys) may be done to rule out any involvement of these structures. Ultrasound can be used to study the kidneys and a CT scan is often very good at studying the entire length of the urinary tract.

More recently, urine-based marker tests are being developed and provide yet another means to complement the methods of the invention. These new tests are non-invasive and accurate in detecting low-grade bladder cancer and therefore are especially useful in monitoring for recurrence. They comprise:

BTA assays (Polymedco, formerly Bard Diagnostics, USA) detects hCFHrp, or human complement factor H-related protein, which is present in the urine of patients with bladder cancer. There are both quantitative and qualitative BTA methods available.

The NMP22 Test Kit (Matritech Inc., Newton, Mass.) detects a nuclear mitotic apparatus (NMA) protein that is abundant in the nuclear matrix. In bladder tumor cells, NMA is elevated and released in detectable levels. There are both quantitative and qualitative NMP22 methods.

The Vysis UroVysion assay (Abbott Molecular Diagnostics) combines urine cytology with molecular (DNA-based) technology to detect the recurrence of cancer. It employs Fluorescence in situ Hybridization (FISH) technology, which uses small, fluorescently-labelled DNA probes to microscopically identify specific regions of DNA.

ImmunoCyt (DiagnoCure) is an immunocytochemistry assay for the detection of Mucin and CEA antigens expressed by tumor cells in the urine of patients previously diagnosed with bladder cancer. This immunofluoresence method is to be combined with urine cytology for the early detection of bladder cancer recurrence. ImmunoCyt is a qualitative assay.

The targeting of multiple DNA alterations may augment efficient cancer identification. Therefore, additional genetic markers may be used in order to supplement the methods of the invention. The genetic markers may concern mutation markers that allow detection of mutations in distinct genes, or, alternatively epigenetic markers that allow detection of DNA methylation in distinct genes.

A combination of the methods of the invention with (urinary) cytology and/or FGFR3 mutation analysis may enhance the sensitivity associated with both cytology and mutation analysis whilst retaining specificity. The methods of the invention may be utilised in combination with urinary cytology and/or mutation analysis in certain embodiments. In specific embodiments the mutation analysis comprises, consists essentiality of or consists of fibroblast growth factor receptor 3 (FGFR3) mutation analysis. FGFR3 mutations have been reported as being very frequent in bladder tumours of low stage and grade. Methods including detecting mutation in FGFR3 may thus be utilised to diagnose, predict etc. superficial or early stage bladder cancer in certain embodiments. Any suitable mutational analysis technique may be employed. In specific embodiments, identification of one or more single nucleotide mutations in the FGFR3 gene is carried out. This may be carried out through use of suitable primer extension assays, such as described by Van Oers et al (Clinical Cancer Research 2005, 11 (21) Nov. 1, 2005) which reference is incorporated herein in its entirety. Primers for use in these methods are set forth as follows:

```
SEQ ID NO: 19  5'-T46CGTCATCTGCCCCCACAGAG-3'

SEQ ID NO: 20  5'-T36TCTGCCCCCACAGAGCGCT-3'

SEQ ID NO: 21  5'-T28TCTGCCCCCACAGAGCGCT-3'

SEQ ID NO: 22  5'-T29GGTGGAGGCTGACGAGGCG-3'

SEQ ID NO: 23  5'-T43ACGAGGCGGGCAGTGTGT-3'

SEQ ID NO: 24  5'-T34CCTGTTCATCCTGGTGGTGG-3'

SEQ ID NO: 25  5'-T50GCACAACCTCGACTACTACAAG-3'

SEQ ID NO: 26  5'-T20CACAACCTCGACTACTACAAGA-3'
```

Thus, the following mutations may be identified: R248C, S249C, G372C, Y375C, A393E, K652E/Q, K652M/T, as shown in the table below. The methods may employ multiplex PCR followed by single nucleotide primer extension using labelled dideoxynucleotides.

Other molecular markers may be additionally or alternatively investigated, such as Ki-67 labelling (MIB-1 staining) in order to supplement the methods of the invention.

Testing can be performed diagnostically or in conjunction with a therapeutic regimen. Epigenetic loss of function of at least one gene selected from FOXE1 and GATA4 can be rescued by the use of DNA demethylating agents and/or DNA methyltransferase inhibitors. Testing can be used to determine what therapeutic or preventive regimen to employ on a patient and be used to monitor efficacy of a therapeutic regimen.

Accordingly, also provided is a method for predicting the likelihood of successful treatment of bladder cancer with a DNA demethylating agent and/or a DNA methyltransferase inhibitor and/or HDAC inhibitor comprising detecting an epigenetic change in at least one gene selected from FOXE1 and GATA4 (in a sample obtained from the subject, as defined herein) wherein detection of the epigenetic change is indicative that the likelihood of successful treatment is higher than if the epigenetic modification is not detected.

Alternatively, the invention provides for a method for predicting the likelihood of resistance to treatment of bladder cancer with a DNA demethylating agent and/or DNA methyltransferase inhibitor and/or HDAC inhibitor comprising detecting an epigenetic change in at least one gene selected from FOXE1 and GATA4 (in a sample obtained from the subject, as detailed herein) wherein detection of the epigenetic change is indicative that the likelihood of resistance to treatment is lower than if the epigenetic modification is not detected.

Epigenetic loss of gene function can identify the need for treatment which may differ according to the type of carcinoma. Therefore, the present invention also relates to a method of selecting a suitable treatment regimen for bladder cancer comprising detecting an epigenetic change in at least one gene selected from FOXE1 and GATA4 (in a sample obtained from the subject, as detailed herein), wherein detection of the epigenetic change results in selection of a DNA demethylating agent and/or a DNA methyltransferase inhibitor and/or a HDAC inhibitor for treatment and wherein if the epigenetic change is not detected, a DNA demethylating agent and/or a DNA methyltransferase inhibitor and/or a HDAC inhibitor is not selected for treatment.

In certain aspects, epigenetic loss of gene function can identify the need for a surgical treatment of a tumour. Accordingly, the invention provides a method for predicting suitable treatment of a bladder cancer, such as a transitional cell carcinoma or squamous cell carcinoma, comprising determining the methylation status of at least one gene selected from FOXE1 and GATA4, in a sample obtained from a subject, wherein if at least one gene is methylated, in particular hypermethylated, the need for resection of the bladder cancer is identified. In such cases, preventive treatment may be recommended and involve resection of the tumour. In the alternative, the invention provides a method for predicting suitable treatment of a bladder cancer, such as a transitional cell carcinoma or squamous cell carcinoma, comprising determining the methylation status at least one gene selected from FOXE1 and GATA4 in a sample obtained from the subject, wherein if the at least one gene is unmethylated or methylated to a lesser degree, it is decided that there is no need for resection of the transitional cell tumor.

In a further related aspect, the invention provides a method of treating bladder cancer in a subject comprising administration of a DNA demethylating agent and/or a DNA methyltransferase inhibitor and/or a HDAC inhibitor wherein the subject has been selected for treatment on the basis of a method of the invention.

For all of the relevant methods (pharmacogenetic methods, treatment regimen methods and methods of treatment) of the invention, the DNA demethylating agent may be any agent capable of up regulating transcription of at least one of the novel tumour suppressor genes. The DNA methyltransferase inhibitor may be any suitable inhibitor of DNA methyltransferase activity or expression which is suitable for treating cancer in the presence of methylation of the at least one gene. The DNA methyltransferase inhibitor may, be one which reduces expression of DNMT genes, such as suitable antisense molecules, or siRNA molecules which mediate RNAi for example. The design of a suitable siRNA molecule is within the capability of the skilled person and suitable molecules can be made to order by commercial entities (see for example, www.ambion.com). In embodiments, the DNA methyltransferase gene is (human) DNMT1.

Alternatively, the agent may be a direct inhibitor of DNMTs. Examples include modified nucleotides such as phosphorothioate modified oligonucleotides (FIG. 6 of Villar-Garea, A. And Esteller, M. DNA demethylating agents and chromatin-remodelling drugs: which, how and why? Current Drug Metabolism, 2003, 4, 11-31) and nucleosides and nucleotides such as cytidine analogues. Suitable examples of cytidine analogues include 5-azacytidine, 5-aza-2'-deoxycytidine, 5-fluouro-2'-deoxycytidine, pseudoisocytidine, 5,6-dihydro-5-azacytidine, 1-β-D-arabinofuranosyl-5-azacytosine (known as fazabarine) (see FIG. 4 of Villar-Garea, A. And Esteller, M. DNA demethylating agents and chromatin-remodelling drugs: which, how and why? Current Drug Metabolism, 2003, 4, 11-31). The DNA methyltransferase inhibitor may comprise Decitabine.

Additional DNMT inhibitors include S-Adenosyl-Methionine (SAM) related compounds like ethyl group donors such as L-ethionine and non-alkylating agents such as S-adenosyl-homocysteine (SAH), sinefungin, (S)-6-methyl-6-deaminosine fungin, 6-deaminosinefungin, N4-adenosyl-N4-methyl-2,4-diaminobutanoic acid, 5'-methylthio-5'-deoxyadenosine (MTA) and 5'-amino-5'-deoxyadenosine (Villar-Garea, A. And Esteller, M. DNA demethylating agents and chromatin-remodelling drugs: which, how and why? Current Drug Metabolism, 2003, 4, 11-31). Useful DNMT inhibitors in the present invention comprise, consists essentially of or consists of 5-azacytidine and/or zebulaine.

Further agents which may alter DNA methylation and which may, therefore, be useful in the present invention as DNA demethylating agents include organohalogenated compounds such as chloroform etc, procianamide, intercalating agents such as mitomycin C, 4-aminobiphenyl etc, inorganic salts of arsenic and selenium and antibiotics such as kanamycin, hygromycin and cefotaxim (Villar-Garea, A. And Esteller, M. DNA demethylating agents and chromatin-remodelling drugs: which, how and why? Current Drug Metabolism, 2003, 4, 11-31).

Many HDAC inhibitors are similarly known in the art. Examples include carboxylic acid based HDAC inhibitors such as valproate and/or butyrate and hydroxamic acid based HDAC inhibitors such as trichostatin A, suberoyl hydroxamic acid (SBHA), 6-(3-chlorophenylureido)caproic hydroxamic acid (3-CI-UCHA), m-carboxycinnamic acid bishydroxylamide (CBHA), suberoylanilide hydroxamic acid (SAHA), azelaic bishydroxamic acid (ABHA), pyroxamide, aromatic sulfonamides bearing a hydroxamic acid group and cyclic-hydroxamic-acid containing peptides.

For each of these additional aspects, the embodiments and optional features of the methods of the invention apply mutatis mutandis and are not repeated for reasons of conciseness. Thus, all (variants of the) methods of detecting an epigenetic change in the at least one gene may be employed appropriately.

The invention also provides kits which may be used in order to carry out the methods of the invention. The kits may incorporate any of the preferred features mentioned in connection with the various methods (and uses) of the invention herein.

Thus, a kit is provided for detecting a predisposition to, or the incidence of, bladder cancer in a sample (the sample comprising nucleic acid molecules from bladder cells, as defined herein) comprising at least one primer pair and/or probe for determining the methylation status of each gene in a panel of genes wherein the panel of genes comprises, consists essentially of or consists of a panel of genes selected from FOXE1 and TWIST1; FOXE1, TWIST1 and NID2; FOXE1, CCNA2 and NID2; GATA4 and NID2; GATA4, NID2 and TWIST1; CCNA1, NID2 and GATA4 or FOXE1 and GATA4. As discussed herein, these panels of genes have been shown to be useful in predicting or diagnosing bladder cancer, non-invasively, with excellent sensitivity and specificity. Suitable primer pairs for determining the methylation status of each of the genes of the panel are set forth in table 1. The primers and/or probe may permit direct determination of the methylation status of the panel of genes, for example following bisulphite treatment of the DNA. Thus, they may be MSP or bisulphite sequencing primers for example. The kits may additionally include one or more probes for real-time or end-point detection. Suitable probes are also set forth in table 1. The probes may additionally or alternatively permit direct determination of the methylation status of the panel of genes, for example following bisulphite treatment of the DNA. Blocking probes may also be utilised in certain embodiments, according to the Heavymethyl technique (see Nucleic Acids Res. 2004; 32(i) e10).

The primers and/or probe may investigate an epigenetic change, and in particular the methylation status, of the relevant gene or genes around the TSS, the genomic location of which is shown in Table 1 (based upon publicly available human genome sequence information—from Ensembl) for each of the relevant genes. In certain embodiments, the primers and/or probe may investigate an epigenetic change, and in particular the methylation status within, or between, and optionally including, the primer and/or probe binding sites of the primers and/or probes listed in the table. In specific embodiments, the primers and/or probes may investigate an epigenetic change, and in particular the methylation status, within or between the genomic locations listed in Table 1 (see the column entitled "location of the assay"). Thus, for example, the primers and/or probes may investigate the genomic region between (and including) nucleotide 99655269 and nucleotide 99655174 for FOXE1 and/or the genomic region between (and including) nucleotide 11599063 and nucleotide 11599169 for GATA4.

The kit may further comprise means for processing a urine sample (containing bladder cells or genomic DNA from bladder cells) as discussed herein.

A kit is also provided for detecting a predisposition to, or the incidence of, bladder cancer in a sample (the sample comprising nucleic acid molecules from bladder cells, as defined herein) comprising:
(a) means for detecting an epigenetic change in at least one gene selected from FOXE1 and GATA4
(b) means for processing a urine sample.

The means for detecting the epigenetic change may permit the epigenetic change to be identified directly, for example the means may comprise primers and/or probes that investigate the status of the epigenetic change directly (e.g. MSP primers or Heavymethyl probes).

The kit may comprise means for detecting an epigenetic change in a panel of genes comprising at least one of the genes together with means for detecting an epigenetic change in one, two, three, four or five additional genes, wherein detection of an epigenetic change in at least one of the genes in the panel is indicative of a predisposition to, or the incidence of, bladder cancer. The panel of genes may comprise, consist essentially of or consist of two or three genes in certain embodiments. In some embodiments, the additional genes are selected from TWIST1, NID2 and CCNA1. Each has been shown to be linked to the incidence of bladder cancer (methylation of the gene correlates with the incidence of bladder cancer).

The kit may be based upon a panel of genes which comprises, consists essentially of or consists of a panel of genes selected from:
(i) FOXE1 and TWIST1,
(ii) FOXE1, TWIST1 and NID2,
(iii) FOXE1, CCNA2 and NID2,
(iv) GATA4 and NID2,
(v) GATA4, NID2 and TWIST1,
(vi) CCNA1, NID2 and GATA4 or
(vii) FOXE1 and GATA4

The kits may enable the detection to be carried out in a single reaction, for example by including suitably labelled primers or probes or by selecting amplification products which can be readily distinguished according to size, molecular weight etc. In specific embodiments, the epigenetic change is methylation.

This kit may be for use in MSP and may enable a real-time detection version of MSP. In some embodiments the kit permits an end-point detection version of MSP to be carried out. Thus, the means for detecting an epigenetic change may comprise, consist essentially of or consist of suitable primers for determining whether the at least one gene selected from FOXE1 and GATA4 (together, optionally, with the additional genes) is methylated. These primers may comprise any of the primers discussed in detail in respect of the various methods of the invention which may be employed in order to determine the methylation status of the relevant (at least one) gene, and variants thereof (see table 1).

The kit may further comprise probes for real-time detection of amplification products. The probes may comprise any suitable probe type for real-time detection; non-limiting examples include use of TAQMAN probes and/or MOLECULAR BEACONS probes and/or AMPLIFLUOR primers and/ or FRET probes and/or SCORPION primers and/or oligonucleotide blockers. Such kits for real-time detection may also be used for end-point detection. Gene specific probes are set forth in Table 1.

The primers and/or probes may permit direct determination of the methylation status of the at least one gene in all of the kits of the invention, for example following bisulphite treatment of the (DNA in the) sample, as discussed herein. As examples each of the primers and probes set forth in Table 1 permit direct determination of methylation status. They are specific for a methylated binding sequence and thus will only amplify those sequences containing methylated cytosine residues.

In specific embodiments, the primers and/or probes in the kit are selected from those which comprise, consist essentially of, or consist of primers and/or probes comprising, consisting essentially of, or consisting of the nucleotide sequences set forth in table 1 for the purposes of amplifying methylated or unmethylated DNA (following bisulphite treatment). The primers and/or probes may be labelled as required. FAM and DABCYL are representative examples of fluorescent markers which can participate in FRET to provide a reliable indicator of amplification, as discussed herein. Other fluorophores and quenchers may be employed, in particular as FRET pairs, as desired and as would be appreciated by a skilled person.

The primers and/or probe may investigate an epigenetic change, and in particular the methylation status, of the relevant gene or genes around the TSS, the genomic location of which is shown in Table 1 (based upon publicly available human genome sequence information—from Ensembl) for each of the relevant genes. In certain embodiments, the primers and/or probe may investigate an epigenetic change, and in particular the methylation status within, or between, and optionally including, the primer and/or probe binding sites of the primers and/or probes listed in the table. In specific embodiments, the primers and/or probes may investigate an epigenetic change, and in particular the methylation status, within or between the genomic locations listed in Table 1 (see the column entitled "location of the assay"). Thus, for example, the primers and/or probes may investigate the genomic region between (and including) nucleotide 99655269 and nucleotide 99655174 for FOXE1 and/or the genomic region between (and including) nucleotide 11599063 and nucleotide 11599169 for GATA4.

As indicated herein above, the kit may comprise means for processing a urine sample. Such means for processing a urine sample may comprise a stabilising buffer in certain embodiments. Suitable stabilising buffers are described herein and may incorporate appropriate mixtures of buffering and osmolarity adjustment ingredients. Examples include STABILUR tablets, available from Cargille Labs and preservative tubes available from CellSave (CellSave Preservative Tubes).

The kit may further incorporate reagents for extraction/isolation/concentration/purification of DNA in certain embodiments. In further embodiments, the kit may also incorporate a sealable vessel for collection of a urine sample.

In certain embodiments, the kit of the invention further comprises a reagent which modifies unmethylated cytosine (but not methylated cytosine) or vice versa in detectable fashion. This allows methylated residues to be distinguished from non-methylated residues. In certain embodiments, the reagent converts unmethylated cytosine residues to a different nucleotide (uracil) but methylated residues are not converted. In certain embodiments, the reagent comprises bisulphite, preferably sodium bisulphite but may comprise hydrazine for example.

As discussed, suitable controls may be utilised in order to act as quality control for the methods and be included in the kit of the invention. One example of a suitable internal reference gene, which is generally unmethylated, but may be treated so as to be methylated, is β-actin. The kit of the invention may further comprise primers for the amplification of a control nucleic acid which may comprise at least one gene selected from FOXE1 and GATA4 (or indeed one of the additional genes) in unmethylated and/or methylated form.

The kits of the invention may additionally include suitable buffers and other reagents for carrying out the claimed methods of the invention. In certain embodiments, the kit of the invention further comprises, consists essentially of, or consists of nucleic acid amplification buffers.

The kit may also additionally comprise, consist essentially of or consist of enzymes to catalyze nucleic acid amplification. Thus, the kit may also additionally comprise, consist essentially of or consist of a suitable polymerase for nucleic acid amplification. Examples include those from both family A and family B type polymerases, such as Taq, Pfu, Vent etc.

The various components of the kit may be packaged separately in separate compartments or may, for example be stored together where appropriate.

The kit may also incorporate suitable instructions for use, which may be printed on a separate sheet or incorporated into the kit packaging for example.

The kits of the invention may also incorporate means for detecting mutations in the FGFR3 gene. As discussed above, mutations in this gene are linked to the incidence of bladder cancer and thus complement, in synergistic fashion, the methods of the invention. The means for detecting appropriate mutations may comprise suitable primers, such as those selected from primers comprising, consisting essentially of or consisting of the nucleotide sequences set forth as SEQ ID NO's 19 to 26. These kits may also incorporate other components such as dideoxynucleotides and/or primers for amplifying regions of exons 7, 10 and 15 of the FGFR3 gene, as discussed on page 7744 of Van Oers et al (incorporated herein by reference).

The invention will now be described with respect to the following non-limiting examples.

DESCRIPTION OF THE FIGURES

FIG. 1: Decision tree for methylation status determination in urine samples (from training set 2, training set 3, and prostate cancer patients) and DNA from human mononuclear cells. The β-actin copy number calculated for a sample should be at least 15 otherwise the result is considered as invalid. Each gene has got a specific cut-off which is: 15 for CCNA1; 1 for FOXE1; 10 for GATA4_2; 30 for NID2; 17 for TWIST1. A valid sample is considered methylated if the copy number of the considered gene is equal or above its specific cut-off, otherwise it is considered as unmethylated.

EXPERIMENTAL SECTION

Example 1

A Real-Time MSP Assay for Early Detection of Bladder Cancer

Materials and Methods

Marker identification: In order to identify markers able to detect specifically bladder cancer over other cancer types using urine samples, a screen was initially carried out on tissues. For this screening, several assays corresponding to several genes were tested on cancer tissue samples of various origins. Selected genes were used for establishing a single gene assay or a multi-gene assay when combined with other genes (based upon re-expression profiles of bladder cancerous cell lines).

Marker selection in urine: Selected assays from the screening on tissues were tested on urine samples from training set 2 and set 3 (see below) for evaluation of sensitivity and specificity in diagnosing bladder cancer.

Urine sample collection: For the study on bladder cancer, prospective, randomly collected urine samples from multiple centers in Belgium, UK and The Netherlands were used (BLCa 001 prospective study). In this trial, symptomatic patients, attending a urology clinic and ultimately diagnosed with bladder cancer or other non-malignant urological disorders, provided a urine sample for use in real-time MSP analysis. All study participants received appropriate approval from the relevant ethical committee. Symptomatic patients (who had given their informed consent), attending a urology clinic and ultimately diagnosed with bladder cancer or other non-malignant urological disorders, provided a urine sample for use in real-time MSP and cytology analysis. From this ongoing trial, 513 urine samples were tested. Those included 346 samples from patients with no evidence of cancer and 167 samples from patients covering all stages of bladder cancer, with 92% representing early stage diseases. From this collection, two sets of samples were used: named training set 2 and training set 3. Training set 2 corresponds to DNA from 76 urine samples (38 non-cancerous control samples and 34 cancer samples) while training set 3 corresponds to DNA from 81 urine samples (34 cancer samples and 47 non-cancerous control samples). Urine samples from prostate cancer patients were also collected for specificity controls. Collection was done during the day at the clinic and the samples were subsequently centrifuged in the laboratory (see Urine sample preparation).

Urine sample preparation: The collected urine samples were aliquoted in 50 ml portions for further processing. Concerning the 76 urine samples from urine training set 2 and the urine samples from prostate cancer patients, each 50 ml aliquot was centrifuged within 4 h (of collection) at 3000 g for 10 min. Concerning urine samples from urine training set 3, instead of centrifuging the urine sample within 4 h at 3000 g for 10 min, a stabilizer (Stabilur® tablets, Cargille Laboratories, #40050, 5 tablets per 50 ml urine) was added to the urine at the time of collection. The urine sample was then held at room temperature for 24 h to 72 h before centrifugation. In all cases urine sediments were stored at −20° C. for up to 6 months.

DNA extraction from human mononuclear cells: Blood samples collected from healthy donors were centrifuged and human mononuclear cells were isolated using a ready-made, sterile solution containing Ficoll (Lymphoprep™). DNA was extracted with a phenol/chloroform method: samples were first incubated overnight with 50 to 100 µg/ml of proteinase K (Roche) and 1% SDS final concentration at 48° C., with shaking at 1100 rpm. 1 volume of Phenol:Chloroform: Isoamylalcohol (25:24:1) from Invitrogen was added to 1 volume of sample and the mixture was transferred to a Phase Lock Gel tube (Eppendorf). After thorough mixing, the tubes were centrifuged to separate the phases and recover the nucleic-acid-containing aqueous upper one. Extraction with Phase lock gel tubes was done once again. DNA was precipitated by addition of glycogen (Roche) and then modified using bisulfite treatment as for the DNA extracted from urine samples (see below).

DNA isolation from urine: Prior to DNA isolation of the pellet fraction, the frozen sample was thawed at room temperature and centrifuged at 3000 g for 5 minutes to separate the remaining supernatant (few µl) from the cell debris pellet. Genomic DNA from urine sediments was extracted using a Puregene® kit from Gentra Systems, with modifications according to the urine nature: 700 µl of Cell Lysis Solution (provided with kit) was added to the pellet and further processed according to manufacturer's instructions. DNA was rehydrated adding 45 µl of LoTE (3 mM Tris, 0.2 mM EDTA, pH 8.0) buffer and was incubated during 1 hour shaking at 65° C. followed by overnight shaking at 20° C.

DNA quantification and modification: DNA was quantified using Picogreen® dsDNA quantitation kit (Molecular Probes) following the manufacturer's instructions. Bisulfite conversion of genomic DNA was done using a 96-well plate format EZ DNA methylation kit from Zymo Research. A maximum 1.5 µg of DNA is converted according to the manufacturer's protocol. DNA was eluted in 25 µl of Tris-HCl 1 mM pH8.0 and stored at −80° C. prior use.

Real-time MSP: Converted DNA from samples as well as from in Vitro Methylated DNA (Chemicon International), in Vitro unmethylated DNA (Chemicon International) and from specific cell lines (positive and negative for each assay) were processed in real-time MSP. 2.4 µl of modified DNA (or standards) are used in a 12 µl total volume PCR reaction with the following buffer composition: 16.6 mM (NH4)2SO4, 67 mM Tris (pH 8.8), 6.7 mM MgCl2, 10 mM β-mercaptoethanol. The PCR reaction also contains 5 mM dNTPs (Fermentas); 0.48 unit JumpStart™ Taq DNA Polymerase (Sigma); 216 ng reverse primer; 72 ng sense primer; 0.16 µM Beacon. For the specific primers/beacon combination see Table 1. DNA was amplified with an ABI Prism® 7900HT instrument (Applied Biosystems), with the following Thermal profile for all genes: 95° C. for 5 min, 95° C. for 30 sec, 57° C. for 30 sec, and 72° C. for 30 sec for 45 cycles. Results were analysed with the SDS 2.2.2 Software. Quantification is calculated relative to the amplification of the standards resulting in the standard curve.

TABLE 1

Primer and beacon sequences GATA4_2 assay (also referred to as GATA4 (2) or GATA4 assay)

| Assay reference | Accession number | Amplicon length (bp) | Location* of the TSS | Location* of the assay | Primer/ Beacon ID | Primer/Beacon sequences (5'-3') (Beacon modifications: 5' FAM, 3' DABCYL) | SEQ ID NO |
|---|---|---|---|---|---|---|---|
| β-actin | M28424 NM_001101 | 103 | 5535814 | 5538428- 5538325 | Beacon | CGACTGCGTGTGGGGTGGTGATG GAGGAGGTTTAGGCAGTCG | 1 |
| | | | | | Sense primer | TAGGGAGTATATAGGTTGGGGAA GTT | 2 |

TABLE 1-continued

Primer and beacon sequences GATA4_2 assay (also referred to as GATA4 (2) or GATA4 assay)

| Assay reference | Accession number | Amplicon length (bp) | Location* of the TSS | Location* of the assay | Primer/Beacon ID | Primer/Beacon sequences (5'-3') (Beacon modifications: 5' FAM, 3' DABCYL) | SEQ ID NO |
|---|---|---|---|---|---|---|---|
| | | | | | Anti-Sense primer | AACACACAATAACAAACACAAATT CAC | 3 |
| CCNA1 | NM_003914 | 152 | 35904455 | 35904314-35904466 | Beacon | CGACATGCACGACGCCCCCGAAC CTAACGCATGTCG | 4 |
| | | | | | Sense primer | GTTATGGCGATGCGGTTTC | 5 |
| | | | | | Anti-Sense primer | AACACACAATAACAAACACAAATT CAC | 6 |
| FOXE1 | U89995 | 95 | 99655357 | 99655269-99655174 | Beacon | CGTCTCGTCGGGGTTCGGGCGTA TTTTTTTAGGTAGGCGAGACG | 7 |
| | | | | | Sense primer | TTTGTTCGTTITTCGATTGTTC | 8 |
| | | | | | Anti-Sense primer | TAACGCTATAAAACTCCTACCGC | 9 |
| GATA4_2 | AK097060 NM_002052 | 106 | 11599162 | 11599063-11599169 | Beacon | CGACATGCCTCGCGACTCGAATC CCCGACCCAGCATGTCG | 10 |
| | | | | | Sense primer | AGGTTAGTTAGCGTTTTAGGGTC | 11 |
| | | | | | Anti-Sense primer | ACGACGACGAAACCTCTCG | 12 |
| NID2 | AB009799 | 99 | 51605696 | 51605816-51605915 | Beacon | CGACATGGGTTCGTAAGGTTTGG GGTAGCGGCCATGTCG | 13 |
| | | | | | Sense primer | GCGGTTTTTAAGGAGTTTTATTTT C | 14 |
| | | | | | Anti-Sense primer | CTACGAAATTCCCTTTACGCT | 15 |
| TWIST1 | U80998 NM_000474 | 77 | 19123820 | 19123479-19123376 | Beacon | CGACATGCCGGCGGGGAAGGAA ATCGTTTCGCATGTCG | 16 |
| | | | | | Sense primer | GTTAGGGTTCGGGGCGTTGTT | 17 |
| | | | | | Anti-Sense primer | CCGTCGCCTTCCTCCGACGAA | 18 |

Results:

FOXE1 and GATA4 were selected following the screening on tissues samples of various origin. Specificity and sensitivity of these 2 selected markers as single gene assays or combined with previously identified markers (using re-expression profiles of bladder cancerous cell lines) were evaluated using two set of urine samples (set 2 & set 3) from the BLCa 001 prospective study. The methods differ only in the collection step. For the samples derived from training set 3, a stabilizer (Stabilur® tablets) was added to the urine (see materials and methods). Results of sensitivity and specificity obtained when applying the same cut-off are shown below.

Performance of FOXE1 on Urine Samples from Training set 2 and Training Set 3:

Sensitivity and specificity of FOXE1 single gene assay in diagnosing bladder cancer using urine samples from training set 2 and set 3 are shown in Table 2. The results obtained are 70% sensitivity with 87% specificity on training set 2 and 56% sensitivity with 89% specificity on training set 3, when considering a cut-off of 1 copy.

TABLE 2

FOXE1 single marker assay performance, displaying % specificity and % sensitivity for urine training set 2 and set 3 (applied cut-off for FOXE1: 1 copy; applied cut-off for β-actin: 15 copies)

| Sample groups | Training set 2 FOXE1 (cut-off 1) Sensitivity % (# positive/# total) [95% CI] | Training set 3 FOXE1 (cut-off 1) Sensitivity % (# positive/# total) [95% CI] |
|---|---|---|
| Papilloma | 50% (1/2) | 0% (0/2) |
| Ta | 64% (7/11) | 46% (5/11) |
| Tis | 100% (1/1) | 0% (0/2) |
| T1 | 83% (5/6) | 73% (8/11) |
| T2 | 63% (5/8) | 80% (4/5) |
| Unknown | 80% (4/5) | 67% (2/3) |
| All cancer stages | 70% Sensitivity (23/34) [52-83] | 56% Sensitivity (19/34) [39-73] |
| Controls (symptomatic) | 87% Specificity (5/38) [76-98] | 89% Specificity (5/47) [81-98] |

Performance of GATA4_2 on Urine Samples from Training set 2 and Set 3:

Results of sensitivity and specificity of GATA4_2 assay in diagnosing bladder cancer using urine samples from training set 2 and training set 3 are shown in Table 3. The results obtained are 85% sensitivity with 92% specificity on training set 2 and 77% sensitivity with 100% specificity on training set 3, when considering a cut-off of 10 copies.

TABLE 3

GATA4_2 single marker assay performance, displaying % specificity and % sensitivity for urine training set 2 and set 3 (applied cut-off for GATA4_2: 10 copies; applied cut-off for β-actin: 15 copies)

| Sample groups | Training set 2 GATA4_2 (cut-off 10) Sensitivity % (# positive/# total) [95% CI] | Training set 3 GATA4_2 (cut-off 10) Sensitivity % (# positive/# total) [95% CI] |
|---|---|---|
| Papilloma | 100% (2/2) | 0% (0/2) |
| Ta | 79% (11/14) | 46% (5/11) |
| Tis | 100% (1/1) | 0% (0/2) |
| T1 | 83% (5/6) | 73% (8/11) |
| T2 | 88% (7/8) | 80% (4/5) |
| Unknown | 100% (3/3) | 67% (2/3) |
| All cancer stages | 85% Sensitivity (29/34) [73-97] | 77% Sensitivity (26/34) [62-91] |
| Controls (symptomatic) | 92% specificity (3/38) [84-101] | 100% Specificity (0/47) |

Performance of GATA4 and FOXE1 in a Dual Marker Combination on Urine Samples from Training Set 2 and Set 3:

GATA4 and FOXE1 markers, both identified following the screen on tissue samples from several cancer types were combined together. The results of specificity and sensitivity obtained on both training set of samples are presented in Table 4.

TABLE 4

GATA4 and FOXE1 dual marker assay performances, displaying % specificity and % sensitivity, on urine training set 2 and set 3. Applied cut-offs for each marker are, for GATA4_2: 10 copies and FOXE1: 1 copy.

| Sample groups | Training set 2 GATA4 (10) and FOXE1 (1) Sensitivity % (# positive/# total) [95% CI] | Training set 3 GATA4 (10), and FOXE1 (1) Sensitivity % (# positive/# total) [95% CI] |
|---|---|---|
| Papilloma | 100 (2/2) | 50 (1/2) |
| Ta | 92 (11/12) | 82 (9/11) |
| Tis | 100 (1/1) | 100 (2/2) |
| T1 | 83 (5/6) | 100 (10/11) |
| T2 | 88 (7/8) | 91 (5/5) |
| Unknown | 100 (4/4) | 67 (2/3) |
| All cancer stages | 85% Sensitivity (29/33) [77-99] | 85% Sensitivity (29/34) [73-97] |
| Controls (symptomatic) | 82% Specificity (7/38) [69-94] | 89% Specificity (5/47) [81-98] |

Performance of the GATA4 and FOXE1 dual combination assay on training set 2 & 3 of urine samples show an increase in sensitivity when compared to the FOXE1 single marker assay. When compared to GATA4 single marker assay there is an increase in sensitivity in urine training set 3. However, the specificity is not improved compared to the single marker assay GATA4 and FOXE1

Performance of FOXE1 Marker Panels on Urine Samples from Training Set 2 and Training Set 3:

The FOXE1 marker has also been combined with other markers to increase sensitivity and/or specificity of diagnosis. Results are presented for a dual marker assay in which FOXE1 is combined with TWIST1 (Table 5) and for a three marker assay in which FOXE1 is combined with NID2 and TWIST1 or is combined with NID2 and CCNA1 (Table 6).

TABLE 5

Dual marker assay performance including FOXE1 and TWIST1, displaying % specificity and % sensitivity for urine training set 2 and set 3 (applied cut-off for FOXE1: 1 copy; applied cut-off for TWIST1: 17 copies; applied cut-off for β-actin: 15 copies)

| Sample groups | Training set 2 TWIST1 (17) and FOXE1 (1) Sensitivity % (# positive/# total) [95% CI] | Training set 3 TWIST1 (17), and FOXE1 (1) Sensitivity % (# positive/# total) [95% CI] |
|---|---|---|
| Papilloma | 100 (2/2) | 50 (1/2) |
| Ta | 85 (11/12) | 82 (9/11) |
| Tis | 100 (1/1) | 100 (2/2) |
| T1 | 83 (5/6) | 100 (11/11) |
| T2 | 88 (7/8) | 100 (5/5) |
| Unknown | 100 (4/4) | 100 (3/3) |
| All cancer stages | 91% Sensitivity (30/33) [81-100] | 91% Sensitivity (31/34) [82-101] |
| Controls (symptomatic) | 82% Specificity (7/38) [69-94] | 84% Specificity (7/47) [75-95] |

TABLE 6

Three marker assay performances (FOXE1, NID2 and TWIST1, or FOXE1, CCNA1 and NID2) displaying % specificity and % sensitivity for urine training set 2 and set 3 (applied cut-off for FOXE1: 1 copy; applied cut-off for NID2: 30 copies; applied cut-off for TWIST1: 17 copies; applied cut-off for β-actin: 15 copies)

| Sample groups | Training set 2 TWIST1 (17), NID2 (30), and FOXE1 (1) Sensitivity % (# positive/# total) [95% CI] | Training set 3 TWIST1 (17), NID2 (30), and FOXE1 (1) Sensitivity % (# positive/# total) [95% CI] | Training set 3 CCNA1 (15), NID2 (30), and FOXE1 (1) Sensitivity % (# positive/# total) [95% CI] |
|---|---|---|---|
| Papilloma | 100 (2/2) | 50 (1/2) | 0 (0/2) |
| Ta | 91 (10/11) | 91 (10/11) | 91 (10/11) |
| Tis | 100 (1/1) | 100 (2/2) | 100 (2/2) |
| T1 | 100 (6/6) | 100 (11/11) | 100 (11/11) |
| T2 | 88 (7/8) | 100 (5/5) | 100 (5/5) |
| Unknown | 100 (2/2) | 100 (3/3) | 100 (3/3) |
| All cancer stages | 94% Sensitivity (31/33) [86-100] | 94% Sensitivity (32/34) [86-102] | 91% Sensitivity (31/34) [82-101] |
| Controls (symptomatic) | 82% Specificity (7/38) [69-94] | 83% Specificity (8/47) [72-94] | 87% Specificity (6/47) [78-97] |

Combining FOXE1 with TWIST1 increased the sensitivity from 70% to 91% on training set 2 and from 56% to 91% on training set 3. Additional combination with NID2, increased the sensitivity to 94% on both training set 2 & set 3. The combination of FOXE1 with NID2 and CCNA1 increased the specificity to 87%.

Performance of GATA4 Marker Panels on Urine Samples from Training Set 2 and Set 3:

The GATA4 marker has also been combined with other markers to increase sensitivity and/or specificity of diagnosis. Results are presented for a dual marker assay in which GATA4 is combined with NID2 (Table 7) and for a three marker assay in which GATA4 is combined with NID2 and TWIST1 (Table 8).

TABLE 7

Dual marker assay performance including GATA4 (2) and NID2, displaying % specificity and % sensitivity for urine training set 2 and set 3 (applied cut-off for GATA4 (2): 10 copies; applied cut-off for NID2: 30 copies; applied cut-off for β-actin: 15 copies)

| Sample groups | Training set 2 NID2 (30), and GATA4_2 (10) Sensitivity % (# positive/# total) [95% CI] | Training set 3 NID2 (30), and GATA4_2 (10) Sensitivity % (# positive/# total) [95% CI] |
|---|---|---|
| Papilloma | 100 (2/2) | 50 (1/2) |
| Ta | 86 (12/14) | 91 (10/11) |
| Tis | 100 (1/1) | 100 (2/2) |
| T1 | 100 (6/6) | 91 (10/11) |
| T2 | 88 (7/8) | 80 (4/5) |
| Unknown | 100 (3/3) | 100 (3/3) |
| All cancer stages | 91% Sensitivity (31/34) [82-101] | 88% Sensitivity (30/34) [77-99] |
| Controls (symptomatic) | 92% Specificity (3/38) [84-100] | 96% Specificity (2/47) [90-102] |

TABLE 8

Three marker assay performances, displaying % specificity and % sensitivity, including GATA4(2) with NID2 and TWIST1, on urine training set 2 and set 3; or GATA4(2) with CCNA1 and NID2 on urine training set 3. Applied cut-offs are, for GATA4 (2): 10 copies; NID2: 30 copies; TWIST1: 17 copies; β-actin: 15 copies.

| Sample groups | Training set 2 TWIST1 (17), NID2 (30), and GATA4_2 (10) Sensitivity % (# positive/# total) [95% CI] | Training set 3 TWIST1 (17), NID2 (30), and GATA4_2 (10) Sensitivity % (# positive/# total) [95% CI] | Training set 3 CCNA1 (15), NID2 (30), and GATA4_2 (10) Sensitivity % (# positive/# total) [95% CI] |
|---|---|---|---|
| Papilloma | 100 (2/2) | 50 (1/2) | 50 (1/2) |
| Ta | 93 (13/14) | 91 (10/11) | 91 (10/11) |
| Tis | 100 (1/1) | 100 (2/2) | 100 (2/2) |
| T1 | 100 (6/6) | 100 (11/11) | 100 (11/11) |
| T2 | 88 (7/8) | 100 (5/5) | 100 (5/5) |
| Unknown | 100 (3/3) | 100 (3/3) | 100 (3/3) |
| All cancer stages | 94% Sensitivity (32/34) [86-102] | 94% Sensitivity (32/34) [86-102] | 94% Sensitivity (32/34) [86-102] |
| Controls (symptomatic) | 92% Specificity (3/38) [84-100] | 89% Specificity (5/47) [81-98] | 96% Specificity (2/47) [90-102] |

Combining GATA4_2 with NID2 increased the sensitivity from 85% to 91% on training set 2 and from 77% to 88% on training set 3. Adding TWIST1 to this combination increased further the sensitivity to 94%. The combination of GATA4_2 with CCNA1 and NID2 results in an assay sensitivity of 94% and a specificity of 96%.

Bladder Cancer Specificity of FOXE1 and GATA4 Assay 20 urine samples from patients diagnosed with prostate cancer were used for a specificity study and treated in the same way as the other urine samples (training set 2 & 3). Results are shown in Table 9. For each marker, positive controls (one cell line DNA & in vitro methylated DNA) and negative controls (one cell line DNA & in vitro unmethylated DNA) were used. Positive controls were found to be methylated. Among the valid prostate cancer urine samples (actin copy number at least 15), none were detected with the CCNA1, FOXE1, GATA_2, NID2 or TWIST1 assays resulting in a 100% specificity (for bladder cancer) of these 5 individual assays on the samples tested.

TABLE 9

Methylation status summary table of CCNA1, FOXE1, GATA4, TWIST1 and NID2 genes for 20 urine samples (161520_A to 161539_A) from prostate cancer patients and in vitro methylated DNA (IVM), in vitro unmethylated DNA (IVU a & IVU b).

| Sample identification | β-actin copies | CCNA1 | FOXE1 | GATA4_2 | TWIST1 | NID2 |
|---|---|---|---|---|---|---|
| 161520_A | 0.00 | I | I | I | I | I |
| 161521_A | 1380.76 | U | U | U | U | U |
| 161522_A | 437.04 | U | U | U | U | U |
| 161523_A | 484.02 | U | U | U | U | U |
| 161524_A | 1503.35 | U | U | U | U | U |
| 161525_A | 207.09 | U | U | U | U | U |
| 161526_A | 15.90 | U | U | U | U | U |
| 161527_A | 52.02 | U | U | U | U | U |
| 161528_A | 11.92 | I | I | I | I | I |
| 161529_A | 7100.24 | U | U | U | U | U |
| 161530_A | 15.81 | U | U | U | U | U |
| 161531_A | 1216.27 | U | U | U | U | U |
| 161532_A | 3669.87 | U | U | U | U | U |
| 161533_A | 5.57 | I | I | I | I | I |
| 161534_A | 132.98 | U | U | U | U | U |
| 161535_A | 1194.67 | U | U | U | U | U |
| 161536_A | 0.00 | I | I | I | I | I |
| 161537_A | 1630.61 | U | U | U | U | U |
| 161538_A | 13.85 | I | I | I | I | I |
| 161539_A | 1838.88 | U | U | U | U | U |
| IVM | 3952.14 or 4848.55 | M | M | M | M | M |
| IVU a | 5280.21 or 12076.28 | U | U | U | U | U |

TABLE 9-continued

Methylation status summary table of CCNA1, FOXE1, GATA4, TWIST1 and NID2 genes for 20 urine samples (161520_A to 161539_A) from prostate cancer patients and in vitro methylated DNA (IVM), in vitro unmethylated DNA (IVU a & IVU b).

| Sample identification | β-actin copies | CCNA1 | FOXE1 | GATA4_2 | TWIST1 | NID2 |
|---|---|---|---|---|---|---|
| IVU b | 150.02 or 327.78 | U | U | U | U | U |
| Specificity % | | 100 | 100 | 100 | 100 | 100 |

Methylation status for specific positive and negative cell lines are not shown. Based on the decision tree (FIG. 1), samples were classified as methylated (M), un-methylated (U) or invalid (I) (<15 copies of β-actin). After excluding invalid samples, the specificity is 100% for each assay.

In order to control for the specificity of the assays on urine samples containing lymphocytes or other immune cells in case of inflammation of the bladder for example, assays were performed on genomic DNA from human mononuclear cells. Methylation status was established, based on the decision tree shown in FIG. 1. Obtained specificity results are indicated in Table 10.

TABLE 10

Specificity of the assays on genomic DNA from human mononuclear cells of healthy donors.

| Gene | Specificity (%) |
|---|---|
| CCNA1 | 100 |
| FOXE1 | 79 |
| GATA4 | 93 |
| NID2 | 97 |
| TWIST1 | 97 |

The assay performed on genomic DNA from human mononuclear cells of healthy donors, shows that CCNA1 has a specificity of 100%. High specificity, of between 79% and 97%, is obtained with the other markers (FOXE1, GATA4_2, NID2, TWIST1). Thus, in only a small number of samples, could the results be influenced by the presence of lymphocytes in urine. The three most specific markers on human mononuclear cells are CCNA1 (100%), TWIST1 (97%) and NID2 (97%).

CONCLUSION

FOXE1 and GATA4 are both specific and sensitive markers for bladder cancer. Combining these two markers may result in an increased sensitivity and/or specificity in certain samples. When either FOXE1 or GATA4 is combined with other markers (identified using re-expression profiles of bladder cancerous cell lines) an increase in sensitivity and/or specificity has been observed. Indeed, combining FOXE1 with one (TWIST1) or two other markers (TWIST1 and NID2) increased the sensitivity of the assays for both training set 2 and set 3 of samples. The same was observed with GATA4, when combined with one marker (NID2) or two markers (NID2 and TWIST1). A three marker panel including CCNA1 (FOXE1, NID2, CCNA1 or GATA4_2, NID2, CCNA1) resulted in an increase in specificity compared to the three marker panel combination with TWIST1 (FOXE1, NID2, TWIST1 or GATA4_2, NID2, TWIST1). Considering the specific cut-offs applied, the best result was obtained for the three marker panel GATA4, CCNA1 and NID2 with 94% Sensitivity and 96% Specificity.

Assays were performed on urine samples from prostate cancer patients to evaluate their specificity towards diagnosis of bladder cancer. It was observed that CCNA1, FOXE1, GATA4, NID2 and TWIST1 are 100% specific (when excluding invalid samples). It is very unlikely that prostate cancer patients will be mis-diagnosed with bladder cancer using these assays (and specific cut-off). The influence of inflammation or blood in urine could affect 0 to 11% of the samples containing cells or DNA of leucocytes origin. Therefore, results will not be affected for the large majority of urine samples.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method comprising:
   (a) treating genomic DNA from bladder cells in a urine sample with a reagent which selectively modifies unmethylated cytosine residues in the genomic DNA to produce modified residues but which does not modify methylated cytosine residues;
   (b) amplifying the treated genomic DNA with primers comprising SEQ ID NO: 11 and SEQ ID NO: 12 to determine the methylation status of the GATA4 gene; and
   (c) detecting hypermethylation of the GATA4 gene.

2. The method of claim 1 which comprises determining the methylation status of a panel of genes comprising the GATA4 gene together with one, two, three, four or five additional genes, and detecting methylation in at least one of the additional genes in the panel.

3. The method of claim 2 wherein the additional genes are selected from TWIST1, NID2 and CCNA1.

4. The method of claim 2 wherein the panel of genes comprises, consists essentially of or consists of a panel of genes selected from FOXE1 and TWIST1; FOXE1, TWIST1 and NID2; FOXE1, CCNA2 and NID2; GATA4 and NID2; GATA4, NID2 and TWIST1; CCNA1, NID2 and GATA4 or FOXE1 and GATA4.

5. The method of claim 1 wherein a stabilising buffer is added to the urine sample once collected, thus permitting the sample to be stored for a period of up to 72 hours at room temperature without the need for centrifugation of the sample.

6. The method of claim 1 which utilises a probe comprising the nucleotide sequences of SEQ ID NO: 10 (GATA4) in order to determine the methylation status.

7. A method comprising:
(a) isolating genomic DNA from a urine sample comprising bladder cells and treating the genomic DNA with a reagent which selectively modifies unmethylated cytosine residues in the genomic DNA to produce modified residues but which does not modify methylated cytosine residues;
(b) amplifying the treated genomic DNA with primers comprising SEQ ID NO: 11 and SEQ ID NO: 12 to determine the methylation status of the GATA4 gene; and
(c) detecting hypermethylation of the GATA4 gene.

8. The method of claim 7 which comprises determining the methylation status of a panel of genes comprising the GATA4 gene together with one, two, three, four or five additional genes, and detecting methylation in at least one of the additional genes in the panel.

9. The method of claim 8 wherein the additional genes are selected from TWIST1, NID2 and CCNA1.

10. The method of claim 8 wherein the panel of genes comprises, consists essentially of or consists of a panel of genes selected from FOXE1 and TWIST1; FOXE1, TWIST1 and NID2; FOXE1, CCNA2 and NID2; GATA4 and NID2; GATA4, NID2 and TWIST1; CCNA1, NID2 and GATA4 or FOXE1 and GATA4.

11. The method of claim 7 wherein a stabilising buffer is added to the urine sample once collected, thus permitting the sample to be stored for a period of up to 72 hours at room temperature without the need for centrifugation of the sample.

12. The method of claim 7 which utilises a probe comprising the nucleotide sequences of SEQ ID NO: 10 (GATA4) in order to determine the methylation status.

* * * * *